United States Patent
Wilson et al.

(10) Patent No.: US 10,774,049 B2
(45) Date of Patent: Sep. 15, 2020

(54) PU.1 INHIBITORS

(71) Applicants: Albert Einstein College of Medicine, Bronx, NY (US); Georgia State University Research Foundation, Inc., Atlanta, GA (US)

(72) Inventors: W. David Wilson, Atlanta, GA (US); David W. Boykin, Atlanta, GA (US); Gregory Poon, Lawrenceville, GA (US); Ulrich Steidl, New Rochelle, NY (US); Iléana Anthony-Debré, Paris (FR)

(73) Assignees: Albert Einstein College of Medicine, Bronx, NY (US); Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 16/227,739

(22) Filed: Dec. 20, 2018

(65) Prior Publication Data

US 2019/0112276 A1    Apr. 18, 2019

Related U.S. Application Data

(63) Continuation-in-part of application No. PCT/US2017/038647, filed on Jun. 22, 2017.

(60) Provisional application No. 62/353,669, filed on Jun. 23, 2016.

(51) Int. Cl.
| | |
|---|---|
| C07D 209/12 | (2006.01) |
| C07D 235/18 | (2006.01) |
| C07D 235/20 | (2006.01) |
| C07D 401/12 | (2006.01) |
| C07D 401/14 | (2006.01) |
| C07D 409/04 | (2006.01) |
| C07D 421/14 | (2006.01) |
| A61P 35/02 | (2006.01) |

(52) U.S. Cl.
CPC ............ C07D 235/20 (2013.01); A61P 35/02 (2018.01); C07D 209/12 (2013.01); C07D 235/18 (2013.01); C07D 401/12 (2013.01); C07D 401/14 (2013.01); C07D 409/04 (2013.01); C07D 421/14 (2013.01)

(58) Field of Classification Search
CPC .. C07D 209/12; C07D 235/18; C07D 235/20; C07D 401/12; C07D 401/14
See application file for complete search history.

(56) References Cited

U.S. PATENT DOCUMENTS

| | | |
|---|---|---|
| 5,935,982 A | 8/1999 | Dykstra et al. |
| 2012/0059003 A1 | 3/2012 | Bushweller et al. |
| 2014/0142147 A1 | 5/2014 | Henary et al. |

FOREIGN PATENT DOCUMENTS

| | | | | |
|---|---|---|---|---|
| CN | 103524396 A | * | 1/2014 | ........... C07D 209/12 |

OTHER PUBLICATIONS

Chemical Abstracts Registry No. 500714-77-2, indexed in the Registry file on STN CAS Online Mar. 26, 2003. (Year: 2003).*
Timm et al., Parasitology, 2014, 141(10), pp. 1272-1276. (Year: 2014).*
Hu et al., Bioorganic & Medicinal Chemistry Letters, 19(13), 2009, pp. 3374-3377. (Year: 2009).*
Balzarini et al., Investigational New Drugs, 1983, 1(2), pp. 103-115. (Year: 1983).*
An English machine translation of CN 103524396 A, Hu et al., 2014. (Year: 2014).*
PCT International Search Report and Written Opinion dated Nov. 8, 2017 for PCT International Patent Application No. PCT/EP2017/038647, 10 pages.

* cited by examiner

*Primary Examiner* — Laura L Stockton
(74) *Attorney, Agent, or Firm* — Fox Rothschild LLP

(57) ABSTRACT

Disclosed herein are inhibitors of PU.1. The inhibitors are useful for treating disorders associated with abnormal PU.1 levels and function.

27 Claims, 7 Drawing Sheets

Specification includes a Sequence Listing.

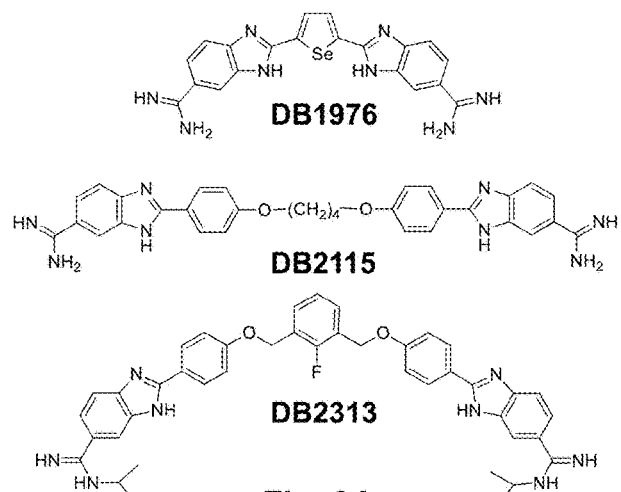
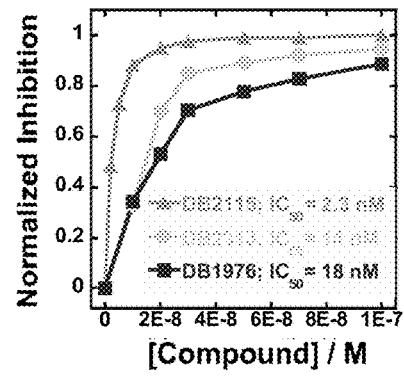
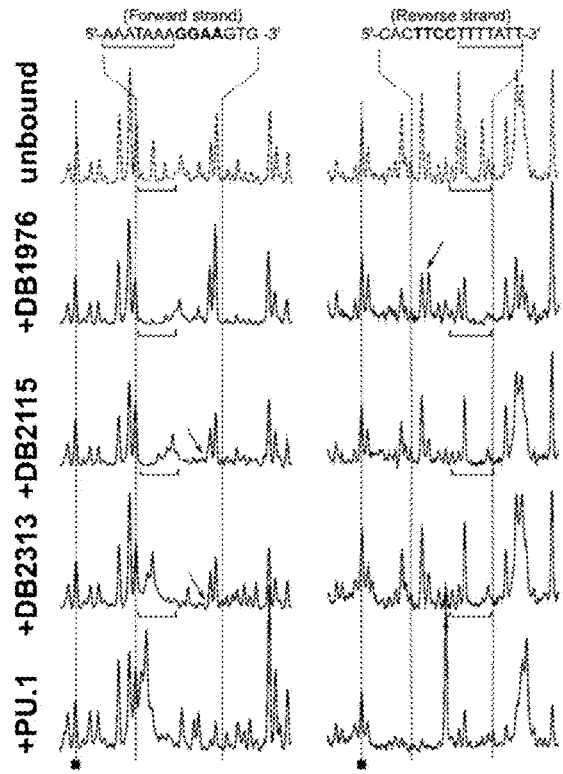
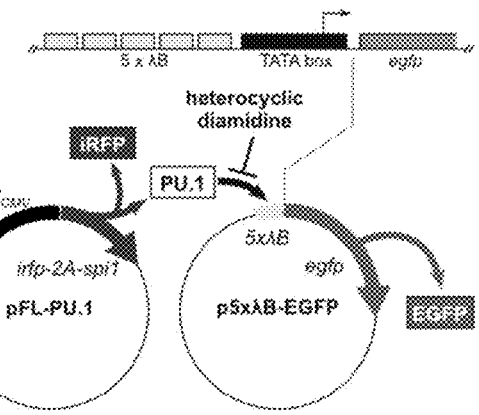
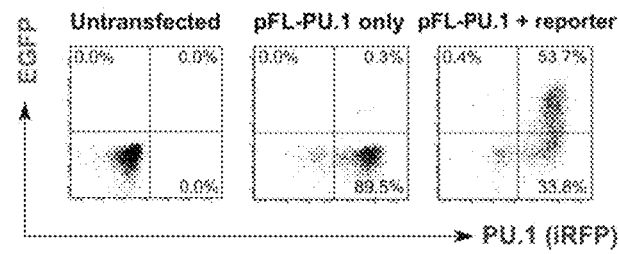
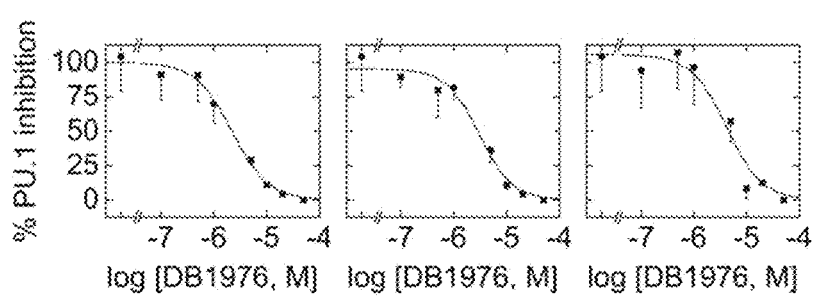
Fig. 2A
Fig. 2B
Fig. 2C
Fig. 2D
Fig. 2E
Fig. 2F

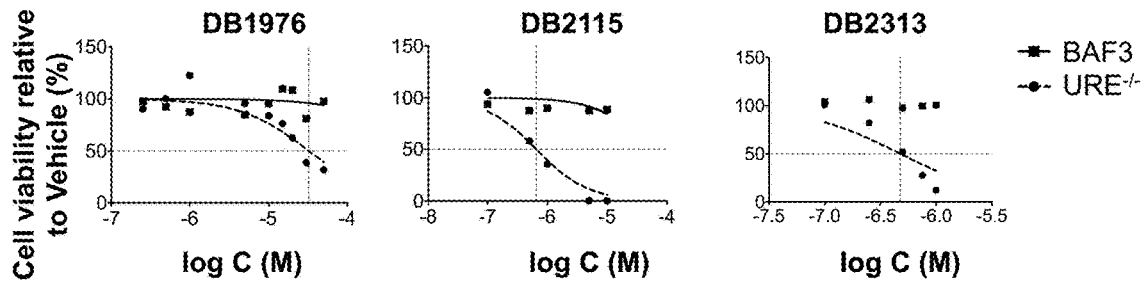
Fig. 3A
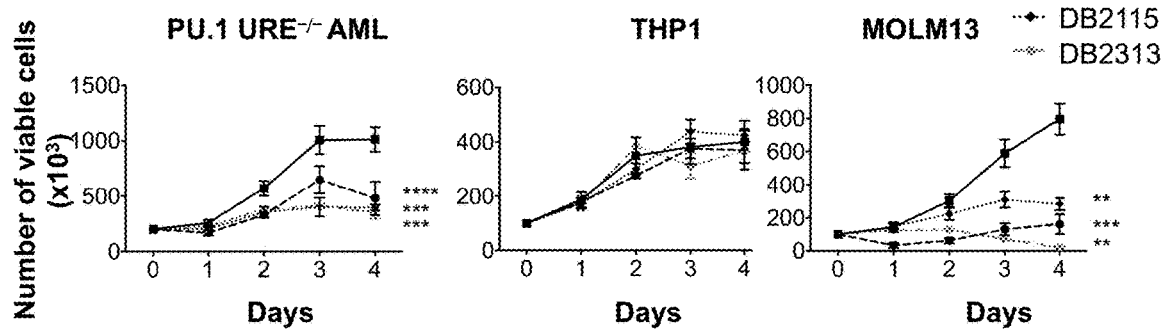
Fig. 3B
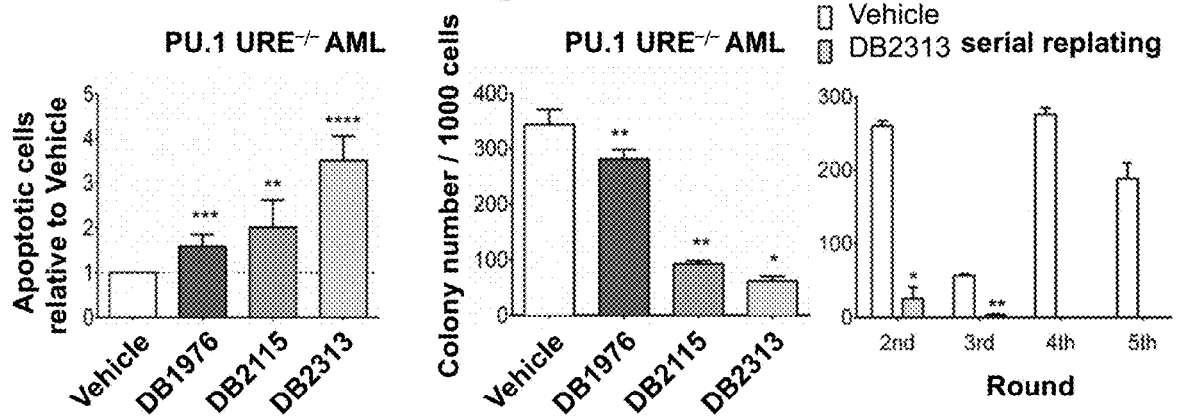
Fig. 3C    Fig. 3D
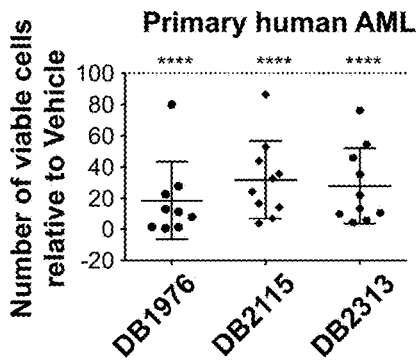  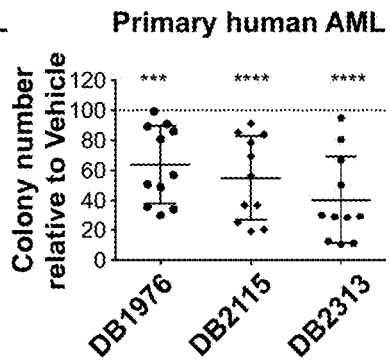  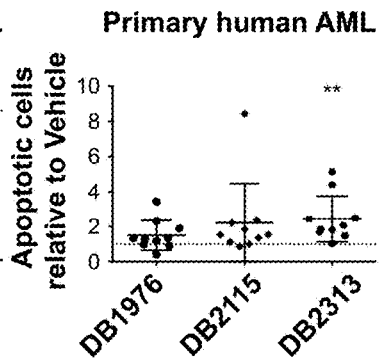
Fig. 3E    Fig. 3F    Fig. 3G

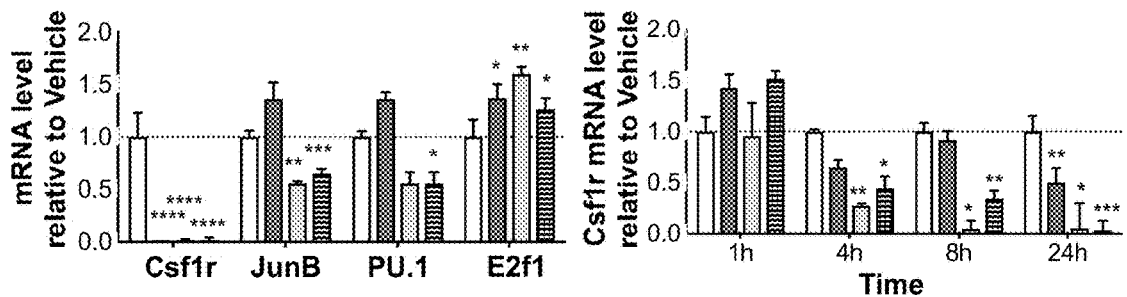
Fig. 4A

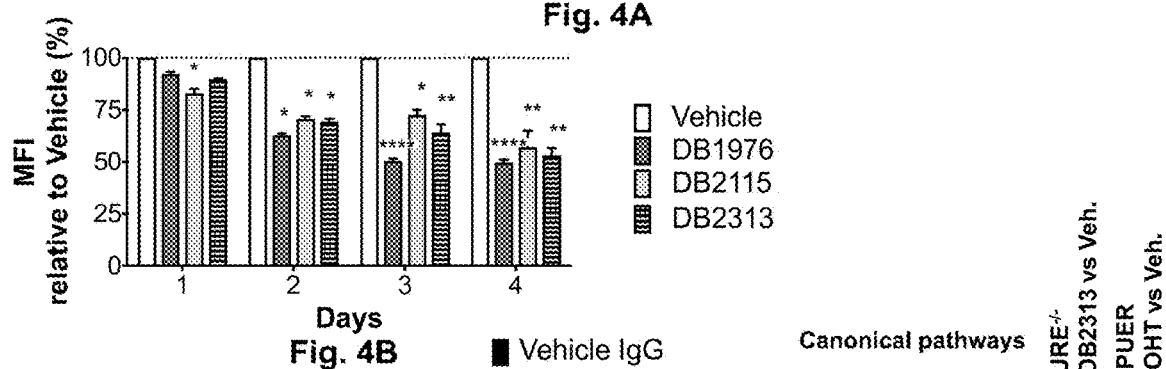
Fig. 4B

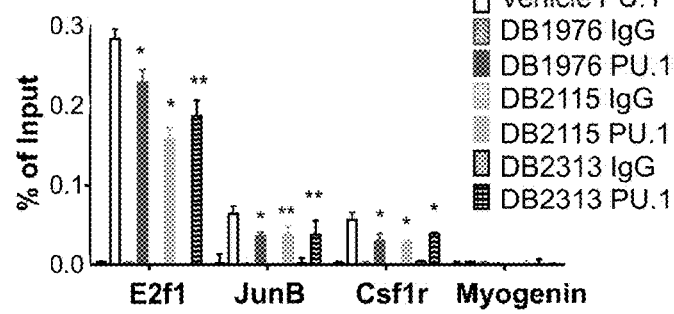
Fig. 4C

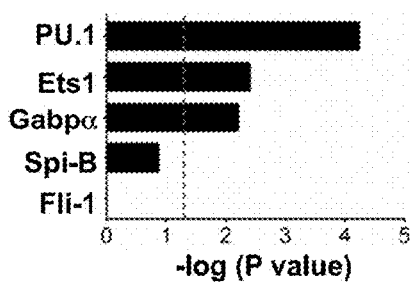
Fig. 4D

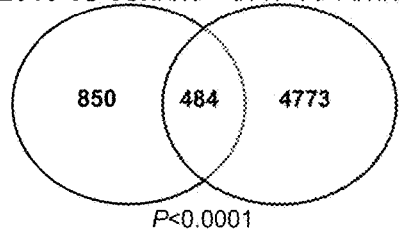
Fig. 4E

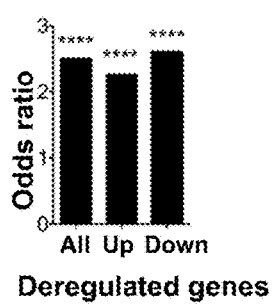
Fig. 4G

| Canonical pathways | URE-/- DB2313 vs Veh. | PUER OHT vs Veh. |
|---|---|---|
| TREM1 Signaling | -1.0 | 3.8 |
| Macropinocytosis Signaling | -1.0 | 3.4 |
| Toll-like Receptor Signaling | -1.9 | 2.2 |
| Integrin Signaling | -1.7 | 2.3 |
| NF-KB Signaling | -1.5 | 2.2 |
| AMPK Signaling | -0.4 | 3.1 |
| Phospholipase C Signaling | -1.3 | 2.1 |
| VEGF Signaling | -2.0 | 1.3 |
| fMLP Signaling in Neutrophils | -0.4 | 2.7 |
| Leukocyte Extravasation Signaling | -0.8 | 2.3 |
| Role of NFAT in Regulation of the Immune Response | -1.0 | 2.0 |
| Tec Kinase Signaling | 0.6 | 2.4 |
| IL-6 Signaling | -0.3 | 2.4 |
| Induction of Apoptosis by HIV1 | 0.3 | -2.2 |
| | Activation z-score | |

Fig. 4F

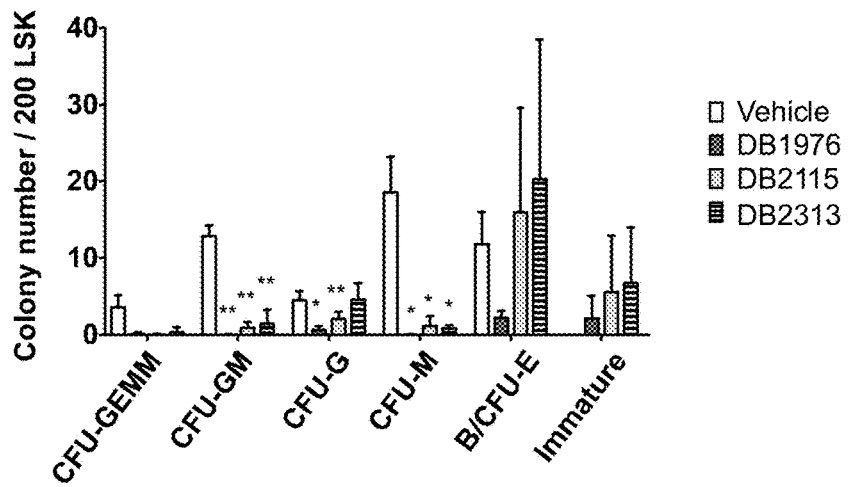
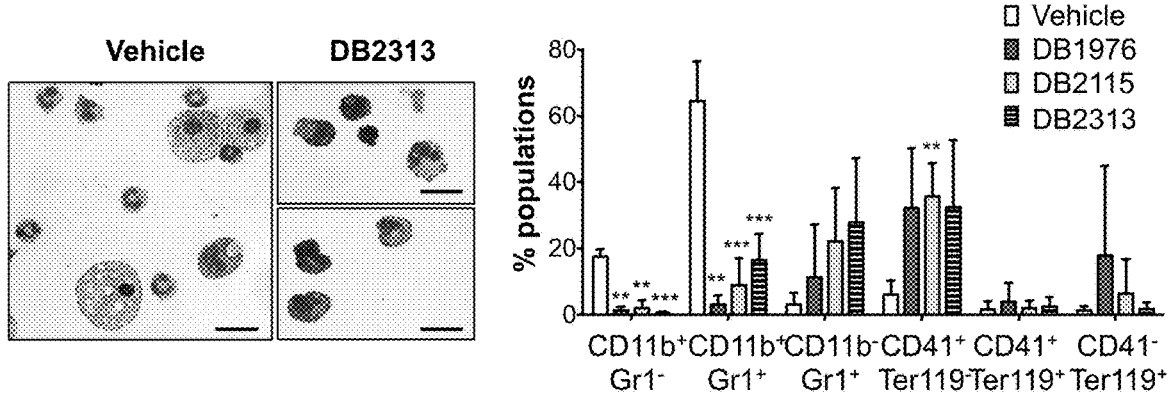
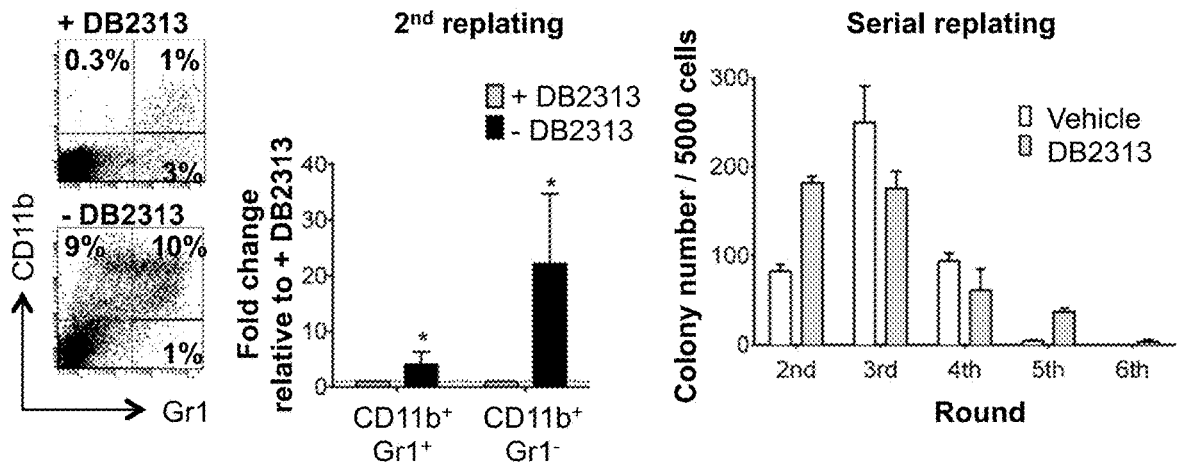
Fig. 5A
Fig. 5B
Fig. 5C
Fig. 5D
Fig. 5E
Fig. 5F Reagents and conditions: a) 4-hydroxybenzaldehyde, $K_2CO_3$, DMF, rt
b) 3,4-diamino-*N*-(i-propyl)benzene-1- carboximidamide, benzoquinone, ethanol, reflux.

PU.1 INHIBITORS

CROSS-REFERENCE TO RELATED APPLICATIONS

This application is a continuation-in-part of and claims priority of PCT International Patent Application No. PCT/US2017/038647, filed on Jun. 22, 2017, which designates the United States of America and which claims the benefit of U.S. Provisional Patent Application No. 62/353,669, filed on Jun. 23, 2016, the contents of which are herein incorporated by reference in their entirety into the present application.

STATEMENT OF GOVERNMENT SUPPORT

This invention was made with government support under grant numbers GM111749 and AI064200 awarded by the National Institutes of Health. The government has certain rights in the invention.

FIELD OF THE INVENTION

This invention relates to novel inhibitors of myeloid master regulator PU.1.

BACKGROUND OF THE INVENTION

ETS (E-Twenty-Six) transcription factors are found throughout the body and play a role in a variety of different physiological functions, including cell differentiation, cell proliferation, apoptosis, angiogenesis, cell migration, and cell cycle control. They are implicated in a wide variety of pathophysiologies, including cancer. One member of the ETS family is designated PU.1, which regulates the expression of receptors such as IL-2Rγ, IL-7Rα and Toll-like receptors. As such, PU.1 is also involved in various autoimmune diseases. Because sequence specific binding is a necessary step in ETS-mediated gene activation, inhibition of the ETS-DNA complex can serve as the pharmacological basis for the treatment of a wide variety of diseases.

Acute myeloid leukemia (AML) is a cancer of the hematopoietic system, characterized by the abnormal clonal proliferation of immature cells, following various genetic and epigenetic alterations. Despite efforts to discover novel therapeutic options, survival in AML remains poor, with a 5-year overall survival of 25%, with overall outcome being worst for patients >60 years of age who represent the vast majority. Especially in this age group, clinical outcome has not significantly improved in the past 4 decades. AML is a genetically very heterogeneous disease, characterized by recurrent genetic mutations which often occur in combination in individual patients (about 30 mutations recur in patients at a frequency of >1%), and on average patients with AML carry a combination of 3-5 'driver mutations'. One of the major challenges facing currently ongoing 'precision oncology' efforts is the low frequency of a larger number of individual mutations and their combinatorial occurrence. Instead of targeting specific genetic aberrations, an alternate strategy for AML treatment would be targeting of more commonly dysregulated pathways that are implicated in various AML subtypes and in larger subsets of patients.

Over the last 15 years, increasing evidence has shown the critical importance of PU.1, an ETS family transcription factor, in AML. A functionally critical decrease in PU.1 level has been described in FLT3-ITD, RUNX1-ETO and promyelocytic leukemia, representing 24, 7 and 13% of all AMLs, respectively (cancer.sanger.ac.uk). Additionally, PU.1 loss of function heterozygous mutations or deletions have been described in AML, and are found in ~10% of MLL-translocated AML. Homozygosity of a single nucleotide variant in an upstream regulatory element (URE) of PU.1, lowering PU.1 expression, has been described in AML with complex karyotype, and a study on highly purified stem cells of patients with AML showed reduced PU.1 levels in at least 40% of examined cases. Overall, disruption of PU.1 expression or activity is present in more than half of AML patients and is associated with a specific transcriptional and epigenetic program, rendering it a very attractive potential therapeutic target.

PU.1 is highly conserved between humans and mice and its functions have been studied using a number of genetically engineered mouse models, which have further proven PU.1's crucial role in hematopoiesis. PU.1 is essential for myeloid and lymphoid lineages, as well as hematopoietic stem cell (HSC) maintenance. Its role in AML development has been firmly established through mouse models with reduced, but not completely absent, PU.1 expression. Homozygous knockout of an enhancer (URE) located −14 kb upstream of PU.1 leads to a decrease in PU.1 expression of 80% and development of a stem cell-derived AML between 3 to 8 months of age. Enhancer haplodeficiency of PU.1 is not sufficient to induce leukemia by itself; however it leads to myeloid bias in stem cells and AML development in combination with cooperating events.

Thus, PU.1 and its downstream transcriptional network are crucial in hematopoiesis and leukemogenesis. AML with disruption of PU.1 function is a distinct entity, associated with specific oncogenes, as well as specific molecular signatures. Thus, targeting PU.1 in AML could be an appealing option for treatment. In the past, strategies to rescue PU.1 expression in AML cells have been explored. Overexpression of PU.1 is sufficient to trigger neutrophil differentiation in acute promyelocytic leukemia (APL), and leads to differentiation and apoptosis of various primary AML samples. Unfortunately, elevation of PU.1 levels or activity is difficult to achieve pharmacologically. However, as complete loss of PU.1 leads to stem cell failure, AML cells may be more vulnerable to further PU.1 inhibition in comparison to normal hematopoietic cells.

In addition to hematologic malignancies, PU.1 is also a promising target in a range of non-malignant diseases with an immunological basis, in which pharmacological inhibition represents a novel therapeutic strategy. The essential role of PU.1 in the differentiation and development of myeloid lineages is well established in mouse and human models of hematopoiesis. PU.1 induces the expression of key receptors such as TLR4 and GM-CSFR, which sensitize granulocytes and monocytes to endotoxins and specific pro-inflammatory cytokines. Thus, PU.1 represents an attractive therapeutic target in non-malignant inflammatory diseases in which granulocytes and monocytes are major cellular mediators. Examples of such diseases that are mediated, at least in part, by granulocytes/monocytes include (but are not restricted to) endotoxemia, rheumatoid arthritis and neurodegenerative diseases.

In mouse models of peritonitis, GM-CSF stimulates differentiation of tissue macrophages and sensitization to bacterial endotoxins (LPS) in a PU.1-dependent manner that strongly correlates with mortality and is markedly attenuated in GMCSF-deficient animals. In other mouse models, endotoxins potently stimulates TLR4 on mature macrophages, leading to local (e.g., lung) and systemic inflammation that is blunted in PU.1-deficient chimeric animals.

The widespread clinical use of anti-TNFα antibodies has highlighted the central role of macrophages/monocytes in RA. Up-regulation of PU.1 is a common feature in activated synovial macrophages and is associated with TLR4 expression. Attention to PU.1 as a therapeutic target in RA is also increasing owing to its regulation of microRNA expression, especially miR-155, a pro-inflammatory RA regulator analogous to its role in AML. A recent observational study has also found elevated PU.1 expression in patients with systemic lupus erythematosus.

Recent evidence has brought to light the immunological basis of chronic neurodegenerative diseases, including Alzheimer's disease. Specifically, microglial proliferation, mediated via the PU.1-target gene csf1r, is associated with neuronal damage and disease progression in mouse models of chronic neurodegeneration. A broader involvement of PU.1 transactivation in microglial development has been identified, and most recently in the specific case of Alzheimer's disease.

In addition to its importance as a myelopoietic regulator, PU.1 also plays an essential role in the function and polarization of certain mature T helper cells. Secretion of IL-9 by Th9 cells, a major cytokine of in allergic inflammation, is transcriptionally controlled by PU.1 following induction by TGFβ. Evidence is rapidly accumulating that IL-9 is the mediator in acute contact dermatitis, asthma, inflammatory bowel disease, pediatric atopy, and giant cell arteritis.

In addition to ensuring the self-renewal of the hematopoietic stem cell (HSC), PU.1 governs cell fate determination in a dosage- and cell-stage dependent fashion. Elevated PU.1 activity is required to drive differentiation of the HSC towards the myeloid lineages (the common myeloid progenitor), at which point continued PU.1 activity induces the terminal development of macrophages and granulocytes, while a tapering of PU.1 activity leads to erythrocytes. At lower concentrations, PU.1 also drives the initial differentiation of the HSC to the common lymphoid progenitor, at which stage a switch in PU.1 dosage induces terminal differentiation into B-(high PU.1) or T-lymphocytes (low PU.1). Since hematopoietic cell fate decisions require multiple transcription factors, often acting in antagonistic fashion [e.g., ↓ PU.1/↑ Ets-1 during T cell development); ↓ PU.1/↑ C/EBPα in regulation of macrophage and neutrophils], PU.1 inhibitors are expected to be useful in a cocktail of other transcriptional modulators, to induce the differentiation of appropriate progenitors into desired cell types. The expected usefulness of PU.1 inhibitors as a cell-reprogramming agent is highlighted by a reversal in PU.1/Ets-1 antagonism in the specialization of mature T cells into subtypes such as Th9.

Typical of ETS-family transcription factors, DNA site recognition by PU.1 requires contact with the major groove, at consensus sites harboring the 5'-GGAA/T-3' sequence specific for the ETS family. Additional contacts with the adjacent DNA minor groove confer selectivity for certain ETS paralogs, such as AT-rich sequences for PU.1. PU.1 inhibitors targeting DNA in the minor groove, by targeting the AT-rich sequences, therefore lead to inhibition of PU.1 binding in the major groove via an allosteric mechanism.

There is a need for novel compounds with enhanced inhibitory potency against PU.1. There is a need for improved methods for treating cancers, including hematologic cancers such as leukemia, as well as other conditions associated with PU.1 dysfunction. The present invention addresses these needs.

SUMMARY OF THE INVENTION

Disclosed herein are compounds capable of inhibiting PU.1. In some instances, the PU.1 inhibitors can be characterized by the following chemical formula:

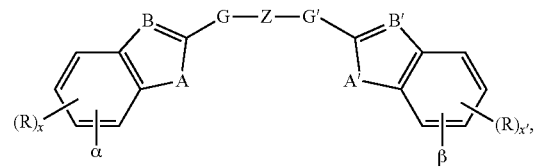

or a pharmaceutically acceptable salt thereof, wherein:

x and x' are each 3;

R is in each case independently selected from $R^a$, $OR^a$, $N(R^a)_2$, $SR^a$, $SO_2R^a$, $SO_2N(R^a)_2$; $COOR^a$, $C(O)N(R^a)_2$, $OC(O)N(R^a)_2$, $N(R^a)C(O)N(R^a)_2$, F, Cl, Br, I, cyano, and nitro, wherein $R^a$ is in each case independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^a$ may together form a ring;

G and G' are independently selected from $C_{3-8}$ cycloalkyl, $C_{2-8}$ heterocyclyl, $C_{6-12}$ aryl, $OC_{6-12}$ aryl, and $C_{3-12}$ heteroaryl, wherein each $C_{6-12}$ aryl or $OC_{6-12}$ aryl is optionally and independently substituted with $R^8$ or $R^9$;

A and A' are independently selected from $NR^1$, O, S, and Se, wherein $R^1$, when present, is in each case independently selected from $R^b$, $SO_2R^b$, $SO_2N(R^b)_2$; $COOR^b$, $C(O)N(R^b)_2$, wherein $R^b$ is in each case independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^1$ may together form a ring;

B and B' are independently selected from N and CR;

α has the formula:

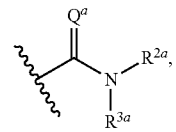

wherein $Q^a$ is O or $NR^{1a}$, wherein $R^{1a}$, $R^{2a}$, and $R^{3a}$ are independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl; wherein any two or more of $R^{1a}$, $R^{2a}$, $R^{3a}$, R and $R^1$ can together form a ring; β has the formula:

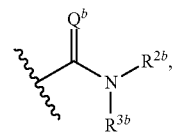

wherein $Q^b$ is O or $NR^{1b}$, wherein $R^{1b}$, $R^{2b}$, and $R^{3b}$ are independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl; wherein any two or more of $R^{1b}$, $R^{2b}$, and $R^{3b}$, R and $R^1$, can together form a ring;

wherein $Q^a$ and $Q^b$ are not both O;

Z is a linking group having the formula:

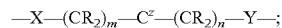

wherein X and Y are independently selected from: a chemical bond; O, S, Se, and $NR^4$; wherein $R^4$, when present, is in each case independently selected from $R^c$, $SO_2R^c$, $SO_2N(R^c)_2$; $COOR^c$, $C(O)N(R^c)_2$, wherein $R^c$ is in each case independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl;

$R_2$ is in each case independently H or F or mixtures thereof;

m and n are each an integer independently selected from 0-4;

$C^z$ is selected from a chemical bond, O, S, Se, $NR^4$, or $C_{2-8}$ heterocyclyl, $C_{6-12}$ aryl, and $C_{3-12}$ heteroaryl;

wherein when X and Y are both 0, $C^z$ is not a chemical bond, and when A" is Se, X and Y are not both a chemical bond;

$R^8$=H or $R^9$;

$R^9$=$O(CH_2)n^aN(R^{10})_2$ or $O(CH_2)n^aNH(C=NH)NH_2$;

$R^{10}$=$C_1$-$C_6$ alkyl or cyclo-alkyl; and $n^a$=2-8.

The compounds disclosed herein are PU.1 inhibitors, and as such can be used to treat diseases associated with abnormal PU.1 activity.

BRIEF DESCRIPTION OF THE DRAWINGS

FIG. 2A-2F. PU.1 inhibition decreases cell growth and increases apoptosis of PU.1$^{low}$ leukemic cells. (A) Chemical structures of heterocyclic diamidines DB1976, DB2115 and DB2313 used in this study. (B) Relative cell viability of URE−/− cells and BAF3 cells after treatment with increasing concentrations of vehicle or small molecules. Cell viability was assessed after 48 h. Data represent means of technical triplicate from one representative experiment; fold change compared to Vehicle is shown. (C) Cell proliferation assay of URE−/− after treatment with DB1976 (n=5), DB2115 (n=3), DB2313 (n=3), of MOLM13 cells (n=3), and THP1 cells (n=3). Cell counting was performed every 24 h during 4 days. Data represent means±SD of technical triplicate from one representative experiment. Forward strand: SEQ ID NO:3, and Reverse strand: SEQ ID NO:4; derived from the λB motif from the murine Ig lambda 2-4 enhancer, a known native PU.1-dependent gene and specific binding site for PU.1. (D) Clonogenic capacities of URE−/− cells after treatment with DB1976 (n=5), DB2115 (n=3) and DB2313 (n=4) in the first plating, and after serial replatings (n=3). Data represent means±SD of technical triplicate from one representative experiment. (E) Apoptotic cells (Annexin-V+Dapi−) fraction in URE−/− cells after 48 h of treatment with DB1976 (n=6), DB2115 (n=6) and DB2313 (n=3). Data represent the means±SD of independent experiments; fold change compared to Vehicle is shown. *P<0.05, P<0.01, *P<0.001, ****P<0.0001 (F) Dose dependent inhibitor of PU.1-dependent transactivation.

FIG. 3A-3G. Novel inhibitors show on-target PU.1 inhibitory activity. (A) Quantitative RT-PCR analysis of Csf1r, Junb, Sfpi1, E2f1 expression after 72 h (n=6) and, for Csf1r, after 1 h (n=3), 4 h (n=7), 8 h (n=3) and 24 h (n=3) of treatment with the small molecules in URE−/− cells, expression is normalized to GAPDH expression. Data represent means±SD of technical triplicate from one representative experiment; fold change compared to Vehicle is shown. (B) Chromatin immunoprecipitation assay showing PU.1 occupancy on E2f1, Junb, Csf1r promoters after treatment in Umsh cell line (n=5). $10 \cdot 10^6$ cells were collected for each condition after 8 h treatment with a double dose of the small molecules (50 uM for DB1976, 1.4 uM for DB2115 and 660 nM for DB2313) or Vehicle; and processed for ChIP using PU.1 monoclonal antibody. Myogenin was used as a negative control, not regulated by PU.1. Data represent means±SD of technical triplicate from one representative experiment. (C) Cell viability after PU.1 rescue in MOLM13 cells. MOLM13 were transduced with a lentiviral construct expressing either PU.1-GFP (PU.1, black bar) or GFP as a control (empty, white bar), sorted on GFP and plated with DB1976 (n=7), DB2115 (n=8), DB2313 (n=6) or Vehicle. Cell count was performed after 4 days. Data represent means±SD of technical triplicate from one representative experiment; fold change compared to Vehicle is shown. (D-G) Transcriptome analysis of URE−/− cells after 24 h of treatment with DB2313 versus vehicle (n=3). Differentially expressed genes were determined with a fold change at 1.2 and a P value <0.1. (D) Enrichment in genes directly regulated by PU.1 or in genes regulated by the other ETS transcription factors Ets1, Gabpa, Spi-B, Fli-1, using Ingenuity Knowledge Base. The red dotted line represents the significance threshold (−log (P value)>1.3). (E,F) Comparison analysis of deregulated genes in URE−/− cells after DB2313 treatment and in PUER cells after PU.1 induction (GSE13125). Deregulated gens in PUER cells were analyzed with a FC at 1.5 and P-value <0.05. (E) Significant overlap between the 2 datasets, with 484 genes commonly deregulated. P-value was calculated using the hypergeometric test. (F) Comparative analysis of deregulated canonical pathways between the 2 datasets (z-score >2 for PUER dataset). Colored squares indicate activation z-score. (G) Enrichment of PU.1 binding at promoters of all, up- and down-deregulated genes after DB2313 treatment. Publically available PU.1 Chip-seq data in PUER cells (GSE63317) has been used for this analysis and promoters defined as −1 kb before TSS. *P<0.05, P<0.01, *P<0.001, ****P<0.0001.

FIG. 4A-4G. PU.1 inhibition decreases cell growth and increases apoptosis of primary human AML cells. (A-C) Transduced GFP+ human primary mononuclear AML cells were plated in semi-solid media (150 000 cells per ml of methyl); colony number, number of viable cells and apoptotic cells were assessed after 14 days of culture. (A, B) Clonogenic capacities and number of viable cells after transduction with shPU.1_1 and shPU.1_2 (n=7). (C) Apoptotic cells (Annexin-V+Dapi−) fraction after transduction with shPU.1_1 and shPU.1_2 (n=7). (D-F) Human primary mononuclear AML cells were plated in semi-solid media (150 000 cells per ml of methyl) containing the PU.1 inhibitors DB1976, DB2115 and DB2313; colony number, number of viable cells and apoptotic cells were assessed after 14 days of culture. (D-E) Clonogenic capacities (n=9) and number of viable cells (n=8) after treatment. (F) Apoptotic cells (Annexin-V+Dapi−) fraction after treatment (n=8). (G) Enrichment of PU.1 binding in up- and down-regulated genes. (A-G) Data represent means±SD, each AML sample is represented by an individual dot. Fold change compared to shCtrl or Vehicle is shown.

FIG. 5A-5F. PU.1 inhibitors decrease the granulo-monocytic potential of hematopoietic stem and progenitor cells, which is rapidly reversible. (A-C) Lin−Sca1+c-Kit+(LSK) cells were plated in semi-solid media containing PU.1 inhibitors. (A) Number of colony-forming unit granulocyte (CFU-G), monocyte (CFU-M), granulo/monocyte (CFU-GM), granulo/erythrocyte/monocyte/megakaryocyte (CFU-GEMM), burst or colony forming unit erythroid (B/CFU-E) and immature colonies after treatment. Detailed histograms of CFU-GM, CFU-G and CFU-M numbers are shown. Data represent the means±SD of 3 independent experiments. (B) Cells coming from colony assays after vehicle or DB2313 treatment. Cells were cytospun and stained with May-Grünwald Giemsa. Scale bar is equal to 20 µm. (C) FACS analysis showing the percentage of CD11b+Gr1−, CD11b+Gr1+, CD11b−Gr1+, CD41+Ter119−, CD41+Ter119+, CD41−Ter119+ populations after colony assays. Data represent the means±SD of 4 independent experiments. (D,E) Cells coming from colony assays treated with DB2313 were replated in the presence (+DB2313) or in the absence of DB2313 (−DB2313) and the percentage of CD11b+Gr1−, CD11b+Gr1+ cells was assessed one week later after culture in semi-solid media. (D) Representative FACS plots (E) Percentage of CD11b+Gr1− and CD11b+Gr1+ populations. Data represent the means±SD of 3 independent experiments; fold change compared to replating with DB2313 is shown. (F) Serial replating assay with D2313 continuous treatment (n=3). Data represent the means±SD of technical triplicate from one representative experiment. *P<0.05, P<0.01, *P<0.001, FIG. 6A-6H. Treatment with PU1 inhibitors increases survival and decreases tumor burden in vivo. (A) Experimental scheme. URE−/− cells were treated in vitro with DB2313 or Vehicle and counted after 2 days of culture. 200·10³ viable cells per mouse were injected retroorbitally into sublethally irradiated mice. Mice were sacrificed at 6 weeks or used for survival analyses. (B) Kaplan-Meier survival analysis of transplanted mice (x animals for vehicle group, xx for DB2313 group, from 2 independent experiments, p=). (C,D) Spleen and liver weight 6 weeks after transplant (8 animals for vehicle group, 7 for DB2313 group). Data represent means±SD, each mouse is represented by an individual dot. (E) Chimerism of URE−/− cells in the bone marrow 6 weeks after transplant (14 animals per group from 2 independent experiments). Data represent means±SD, each mouse is represented by an individual dot. *P<0.05 AML cell engraftment in the bone marrow was significantly decreased after treatment with DB2313, with a mean chimerism of 55% for the vehicle group and 33% for DB2313 group (E, F). Histological analyses revealed severe blast infiltration with disruption of the splenic architecture and virtually complete loss of the red pulp in the vehicle group, and significantly less pronounced effects in the DB2313 group (G). Likewise, infiltration of the liver by leukemic blast was substantially reduced in the DB2313 group in comparison to the vehicle group (H).

DETAILED DESCRIPTION OF THE INVENTION

Figure 1A:
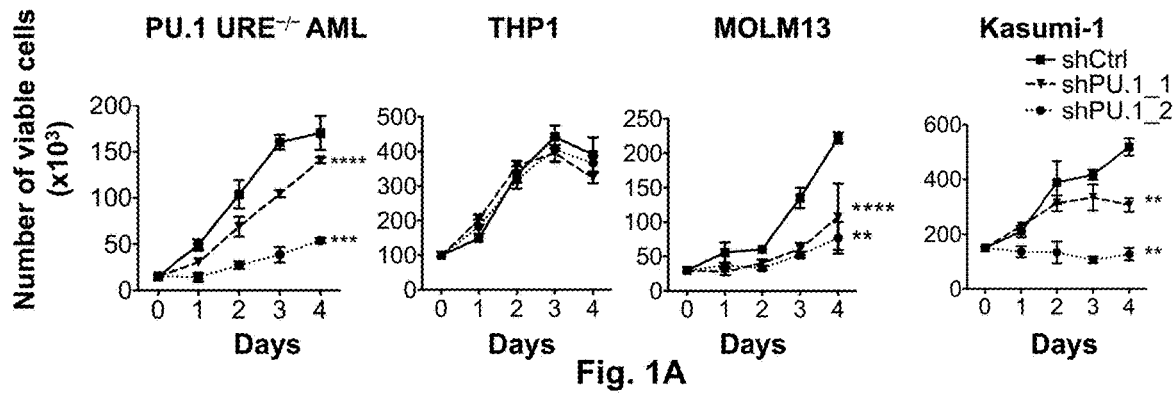
FIG. 1A-1F. PU.1 knockdown decreases cell growth and increases apoptosis of murine and human PU.1$^{low}$ leukemic cells. (A) Cell proliferation assay of URE−/− cells after transduction with shPU.1_1 and shPU.1_2 (n=4). Cell counting was performed every 24 h during 4 days. Data represent means±SD of technical triplicate from one representative experiment. (B) Clonogenic capacities of URE−/− cells after transduction with shPU.1_1 and shPU.1_2 (n=4). Data represent means±SD of technical triplicate from one representative experiment. (C) Apoptotic cells (Annexin-V+Dapi−) fraction in URE−/− cells after transduction with shPU.1_1 and shPU.1_2 (n=3). Data represent the means±SD of independent experiments; fold change compared to shCtrl is shown. (D) Cell proliferation assay in THP1 cells (n=2) and MOLM13 cells (n=3) after transduction with shPU.1_1 and shPU.1_2. Cell counting was performed every 24 h during 4 days. Data represent means±SD of technical triplicate from one representative experiment. (E) Clonogenic capacities of THP1 cells (n=4) and MOLM13 cells (n=6) after transduction with shPU.1_1 and shPU.1_2. Data represent means±SD of technical triplicate from one representative experiment. (F) Apoptotic cells (Annexin-V+Dapi−) fraction in MOLM13 cells after transduction with shPU.1_1 and shPU.1_2 (n=7). Data represent the means±SD of independent experiments; fold change compared to shCtrl is shown. *P<0.05, P<0.01, *P<0.001, ****P<0.0001.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

The term "alkyl" as used herein is a branched or unbranched hydrocarbon group such as methyl, ethyl, n-propyl, isopropyl, n-butyl, isobutyl, t-butyl, pentyl, hexyl, heptyl, octyl, nonyl, decyl, dodecyl, and the like. The alkyl group can also be substituted or unsubstituted. Unless stated otherwise, the term "alkyl" contemplates both substituted and unsubstituted alkyl groups. The alkyl group can be substituted with one or more groups including, but not limited to, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein. An alkyl group which contains no double or triple carbon-carbon bonds is designated a saturated alkyl group, whereas an alkyl group having one or more such bonds is designated an unsaturated alkyl group. Unsaturated alkyl groups having a double bond can be designated alkenyl groups, and unsaturated alkyl groups having a triple bond can be designated alkynyl groups. Unless specified to the contrary, the term alkyl embraces both saturated and unsaturated groups.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is replaced with a heteroatom such as, but not limited to, nitrogen, oxygen, sulfur, selenium or phosphorus. The cycloalkyl group and heterocycloalkyl group can be substituted or unsubstituted. Unless stated otherwise, the terms "cycloalkyl" and "heterocycloalkyl" contemplate both substituted and unsubstituted cycloalkyl and heterocycloalkyl groups. The cycloalkyl group and heterocycloalkyl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein. A cycloalkyl group which contains no double or triple carbon-carbon bonds is designated a saturated cycloalkyl group, whereas an cycloalkyl group having one or more such bonds (yet is still not aromatic) is designated an unsaturated cycloalkyl group. Unless specified to the contrary, the terms cycloalkyl and heterocycloalkyl embrace both saturated and partially unsaturated systems.

The term "aryl" as used herein is an aromatic ring composed of carbon atoms. Examples of aryl groups include, but are not limited to, phenyl and naphthyl, etc. The term "heteroaryl" is an aryl group as defined above where at least one of the carbon atoms of the ring is replaced with a heteroatom such as, but not limited to, nitrogen, oxygen, sulfur, selenium or phosphorus. The aryl group and heteroaryl group can be substituted or unsubstituted. Unless stated otherwise, the terms "aryl" and "heteroaryl" contemplate both substituted and unsubstituted aryl and heteroaryl groups. The aryl group and heteroaryl group can be substituted with one or more groups including, but not limited to, alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein.

Exemplary heteroaryl and heterocyclyl rings include: benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cirmolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The terms "alkoxy," "cycloalkoxy," "heterocycloalkoxy," "cycloalkoxy," "aryloxy," and "heteroaryloxy" have the aforementioned meanings for alkyl, cycloalkyl, heterocycloalkyl, aryl and heteroaryl, further providing said group is connected via an oxygen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless specifically stated, a substituent that is said to be "substituted" is meant that the substituent is substituted with one or more of the following: alkyl, alkoxy, alkenyl, alkynyl, cycloalkyl, heterocycloalkyl, aryl, heteroaryl, aldehyde, amino, carboxylic acid, ester, ether, halide, hydroxy, ketone, nitro, silyl, sulfo-oxo, or thiol as described herein.

Unless specified otherwise, the term "patient" refers to any mammalian animal, including but not limited to, humans.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

Human Transcription factor PU.1 protein (product of the SPI1 gene is) has the following amino acid sequence (SEQ ID NO:1) (UniProtKB-P17947):

```
          10         20         30         40
   MLQACKMEGF PLVPPPSEDL VPYDTDLYQR QTHEYYPYLS 50         60         70         80
   SDGESHSDHY WDFHPHHVHS EFESFAENNF TELQSVQPPQ 90        100        110        120
   LQQLYRHMEL EQMHVLDTPM VPPHPSLGHQ VSYLPRMCLQ 130        140        150        160
   YPSLSPAQPS SDEEEGERQS PPLEVSDGEA DGLEPGPGLL 170        180        190        200
   PGETGSKKKI RLYQFLLDLL RSGDMKDSIW WVDKDKGTFQ 210        220        230        240
   FSSKHKEALA HRWGIQKGNR KKMTYQKMAR ALRNYGKTGE 250        260        270
   VKKVKKKLTY QFSGEVLRGR GLAERRHPPH.
```

A second isoform has been reported where at position 15, P→PQ (SEQ ID NO:2) (UniProtKB-P17947):

```
          10         20         30         40
   MLQACKMEGF PLVPPQPSED LVPYDTDLYQ RQTHEYYPYL 50         60         70         80
   SSDGESHSDH YWDFHPHHVH SEFESFAENN FTELQSVQPP 90        100        110        120
   QLQQLYRHME LEQMHVLDTP MVPPHPSLGH QVSYLPRMCL 130        140        150        160
   QYPSLSPAQP SSDEEEGERQ SPPLEVSDGE ADGLEPGPGL 170        180        190        200
   LPGETGSKKK IRLYQFLLDL LRSGDMKDSI WWVDKDKGTF 210        220        230        240
   QFSSKHKEAL AHRWGIQKGN RKKMTYQKMA RALRNYGKTG 250        260        270
   EVKKVKKKLT YQFSGEVLGR GGLAERRHPP H.
```

Disclosed herein are bis-heterocyclic PU.1 inhibiting compounds. The compounds can be represented by the following Formula 1:

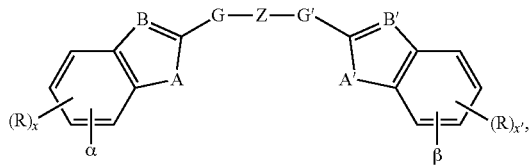

[Formula 1]

or a pharmaceutically acceptable salt thereof, wherein:

x and x' are each 3;

R is in each case independently selected from $R^a$, $OR^a$, $N(R^a)_2$, $SR^a$, $SO_2R^a$, $SO_2N(R^a)_2$; $COOR^a$, $C(O)N(R^a)_2$, $OC(O)N(R^a)_2$, $N(R^a)C(O)N(R^a)_2$, F, Cl, Br, I, cyano, and nitro, wherein $R^a$ is in each case independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^a$ may together form a ring;

G and G' are independently selected from $C_{3-8}$ cycloalkyl, $C_{2-8}$ heterocyclyl, $C_{6-12}$ aryl, $OC_{6-12}$ aryl, and $C_{3-12}$ heteroaryl, wherein each $C_{6-12}$ aryl or $OC_{6-12}$ aryl is optionally and independently substituted with $R^8$ or $R^9$;

A and A' are independently selected from $NR^1$, O, S, and Se, wherein $R^1$, when present, is in each case independently selected from $R^b$, $SO_2R^b$, $SO_2N(R^b)_2$; $COOR^b$, $C(O)N(R^b)_2$, wherein $R^b$ is in each case independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^1$ may together form a ring B and B' are independently selected from N and CR;

α has the formula:

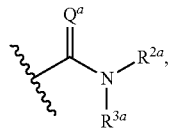

wherein $Q^a$ is O or $NR^{1a}$, wherein $R^{1a}$, $R^{2a}$, and $R^{3a}$ are independently selected from hydrogen, $C_{1-8}$alkyl, $C_{3-8}$ cycloalkyl, or $C_{2-8}$ heterocyclyl; wherein any two or more of $R^{1a}$, $R^{2a}$, $R^{3a}$, R and $R^1$ can together form a ring;

β has the formula:

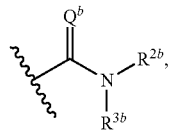

wherein $Q^b$ is O or $NR^{1b}$, wherein $R^{1b}$, $R^{2b}$, and $R^{3b}$ are independently selected from hydrogen, $C_{1-8}$ alkyl, $C_{3-8}$ cycloalkyl, and $C_{2-8}$ heterocyclyl; wherein any two or more of $R^{1b}$, $R^{2b}$, and $R^{3b}$, R and $R^1$ can together form a ring;

wherein $Q^a$ and $Q^b$ are not both O;

Z is a linking group having the formula:

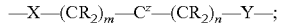

wherein X and Y are independently selected from: a chemical bond; O, S, Se, and $NR^4$; wherein $R^4$, when present, is in each case independently selected from $R^c$, $SO_2R^c$, $SO_2N(R^c)_2$; $COOR^c$, $C(O)N(R^c)_2$, wherein $R^c$ is in each case independently selected from hydrogen, $C_{1-s}$ alkyl, $C_{3-8}$ cycloalkyl, $C_{2-8}$ heterocyclyl, $C_{6-12}$ aryl, and $C_{3-12}$ heteroaryl $R_2$ is in each case independently H or F or mixtures thereof;

m and n are each an integer independently selected from 0-4;

$C^z$ is selected from a chemical bond, O, S, Se, $NR^4$, $C_{3-8}$ cycloalkyl, $C_{2-8}$ heterocyclyl, $C_{6-12}$ aryl, and $C_{3-12}$ heteroaryl;

wherein when X and Y are both O, $C^z$ is not a chemical bond, and when $C^z$ is a selenium containing heterocycle, X and Y are not both a chemical bond;

$R^8$=H or $R^9$;
$R^9$=$O(CH_2)_{n^a}N(R^{10})_2$ or $O(CH_2)_{n^a}NH(C=NH)NH_2$;
$R^{10}$=$C_1$-$C_6$ alkyl or cyclo-alkyl; and
$n^a$=2-8.

In some embodiments, one or both of X and Y are O.

In some instances, B and B' are both N.

In some instances A and A' are both $NR^4$, in which $R^4$ is either hydrogen or $C_{1-4}$ alkyl. In certain embodiments, both of X and Y are O, B and B' are both N, and A and A' are both $NR^4$, in which $R^4$ is either hydrogen or $C_{1-4}$ alkyl.

In certain embodiments, one or both of the α and β groups can be in the 4 position, e.g.:

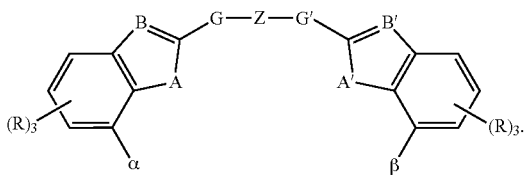

Likewise, in some embodiments, one or both of the α and β groups can be in the 5, 6 or 7 position. In certain embodiments, the phenyl portion of the bicyclic heterocycle portion of the compound may be substituted only with α and β, that is, each of the R groups in those rings is hydrogen, for instance a compound having the formula:

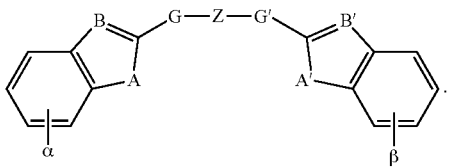

In other embodiments, it is preferred that at least one R group is not hydrogen. For instance, one of the R groups can be an electron donating group in ortho, meta or para position relative to the α or β substituent. Exemplary electron donating groups include $R^a$, $OR^{a\dagger}$, $N(R^a)_2$. In other embodiments, one of the R groups can be an electron withdrawing group in the ortho, meta or para relative to the α or β substituent. Exemplary electron withdrawing groups include $SO_2R^a$, $SO_2N(R^a)_2$; $COOR^a$, $C(O)N(R^a)_2$, $OC(O)N(R^a)_2$, $N(R^a)C(O)N(R^a)_2$, F, Cl, Br, I, cyano, and nitro.

In some cases, G and G' can be an optionally substituted phenyl group or an optionally substituted heteroaryl. G and G' can be independently selected from:

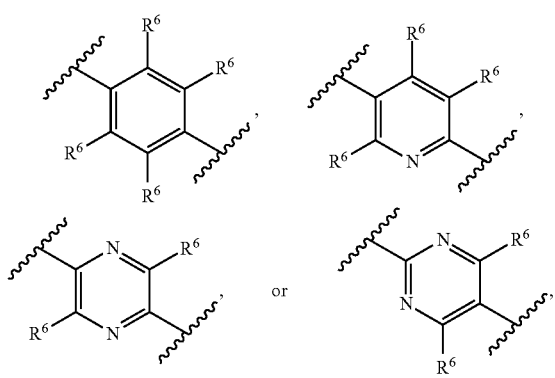

wherein $R^6$ is independently selected from $R^d$, $OR^{d\dagger}$, $N(R^d)_2$, $SR^d$, $SO_2R^d$, $SO_2N(R^d)_2$; $COOR^d$, $C(O)N(R^d)_2$, $OC(O)N(R^d)_2$, $N(R^d)C(O)N(R^d)_2$, F, Cl, Br, I, cyano, and nitro, wherein $R^d$ is in each case independently selected from hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^a$ may together form a ring. In certain embodiments, $R^6$ is in each case hydrogen. In other embodiments, G or G' can be a phenyl or heteroaryl having one or two non-hydrogen groups. In certain cases, the non-hydrogen $R^6$ group can be selected from $R^d$, $OR^{d\dagger}$, $COOR^d$, F, Cl, Br, I, cyano, and nitro.

The four G and G' systems described above can be designated 1,4 systems by virtue that the connectivity pattern in the para configuration. In other embodiments, G and G' can be optionally substituted phenyl, pyridinyl or 1,3 pyrazine group in the 1,3 or 1,2 configuration. When G or G' is a 1,4 pyrazine, the substitution pattern can also be in the 1,2 configuration.

In certain embodiment, α and β are both at the 6 position, and in further embodiments can have an electron withdrawing group at the 4, 5 or 7 position. In some embodiments, α and β are both at the 6 position, and in further embodiments have an electron donating group at the 4, 5, or 7 position.

In certain instances, Z has the formula:

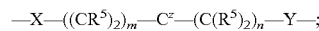

wherein each $R^5$ is independently selected from hydrogen and F, or mixtures thereof. For example, Z can be O—$CH_2$—$CF_2$—$CF_2$—$CF_2$—$CH_2$—O—; O—$CH_2$—$CF_2$—$CF_2$—O—; —O—$CF_2$—$CF_2$—$CF_2$—O—; or —O—$CH_2$—$CF_2$—$CH_2$—O—.

In some embodiments, $C^z$ can be an optionally substituted phenyl or heteroaryl. For instance, $C^z$ can have the formula:

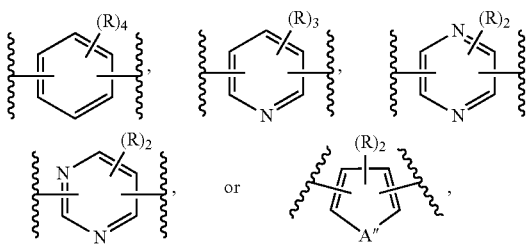

wherein A" is O, S, Se, or $NR^6$; wherein $R^6$ is hydrogen, $C_{1-8}$alkyl; $C_{3-8}$ cycloalkyl, and $C_{2-8}$ heterocyclyl; and in other instances $C^z$ can have the formula:

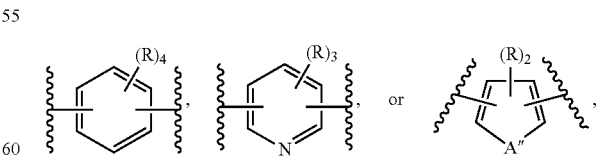

wherein R and A" have the meanings given above. However, when A" is Se, X and Y are not both a chemical bond. In some embodiments, A" can be O. In some embodiments, $C^z$ can be an optionally substituted phenyl or heteroaryl. For instance, $C_z$ can have the formula:

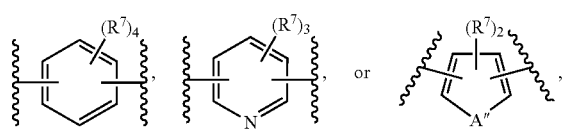

wherein $R^7$ is independently selected from hydrogen, F, Cl, Br, I, cyano or nitro. In some embodiments, $C^z$ can have the formula:

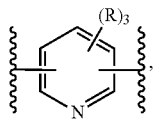

wherein R has the meaning given above. In some embodiments, R can be $R^7$. In certain embodiments, R can be $R^7$, in which $R^7$ is in each case hydrogen. In other embodiments, $C^z$ can be a phenyl group having the formula:

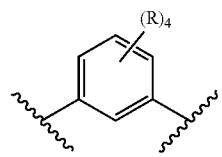

wherein R has the meaning given above. In some embodiments, R can be $R^7$. In certain embodiments, R can be $R^7$, in which $R^7$ is in each case hydrogen. In some cases, $C^z$ can be a phenyl group having the formula:

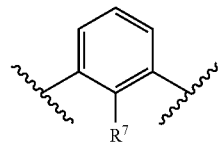

wherein $R^7$ can be R, or can be selected from hydrogen, F, Cl, Br, I, cyano or nitro, preferably F.

$C^z$ can be selected from a chemical bond, O, S, Se, $NR^4$, $C_{3-8}$ cycloalkyl, $C_{2-8}$ heterocyclyl, $C_{6-12}$ aryl, and $C_{3-12}$ heteroaryl or a group of the formula:

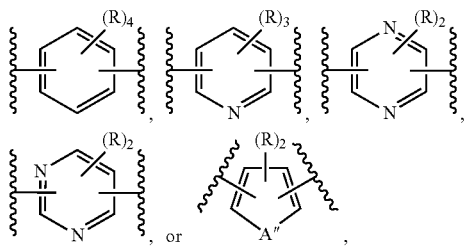

wherein A" is O, S, Se, or $NR^6$; wherein $R^6$ is hydrogen, $C_{1-8}$alkyl; $C_{3-8}$ cycloalkyl, and $C_{2-8}$ heterocyclyl, wherein when X and Y are both O, $C^z$ is not a chemical bond, and when A" is Se, X and Y are not both a chemical bond.

In some embodiments, α has the formula:

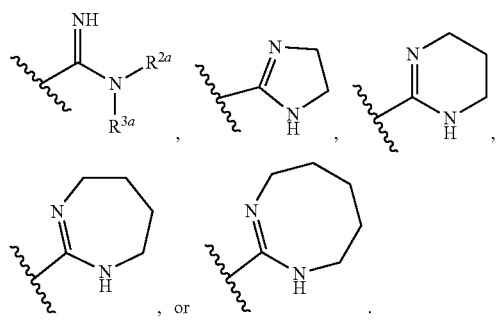

In some embodiments, β has the formula:

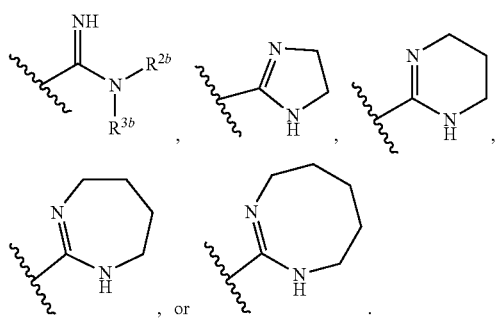

In some embodiments, The compound has the formula

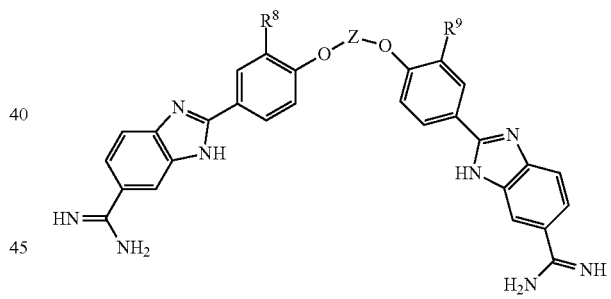

wherein
$R^8$=H or $R^9$;
$R^9$=O(CH$_2$)n$^a$N(R$^{10}$)$_2$ or O(CH$_2$)n$^a$NH(C=NH)NH$_2$;
$R^{10}$=C$_1$-C$_6$ alkyl or cyclo-alkyl; and
$n^a$=2-8.

In one embodiment, $R^8$=H and $R^9$=O(CH$_2$)n$^a$N(R$^{10}$)$_2$. In one embodiment, both $R^8$ and $R^9$=O(CH$_2$)n$^a$N(R$^{10}$)$_2$. In one embodiment, $R^8$=H and $R^9$=O(CH$_2$)n$^a$NH(C=NH)NH$_2$. In one embodiment, both $R^8$ and $R^9$=O(CH$_2$)n$^a$NH(C=NH)NH$_2$.

Figure 8A:
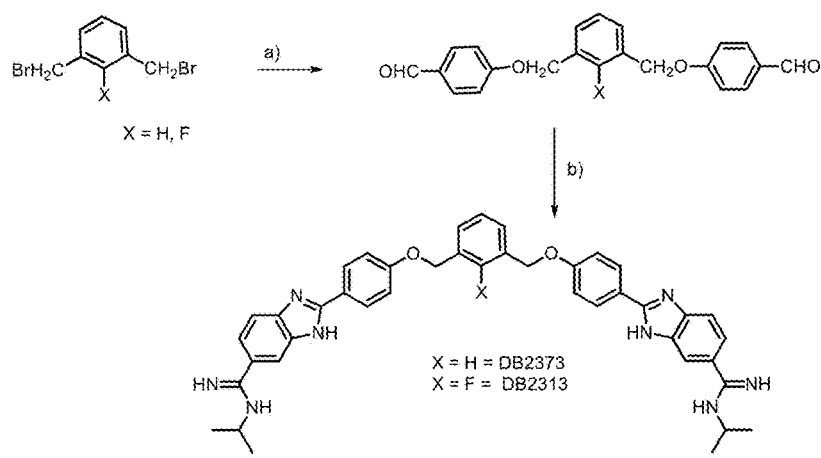
FIG. 8A-8C depicts (A) DB2313 synthesis (B-C) Representative SPR sensorgrams for compounds binding to the immobilized λB promoter DNA sequence: (B) DB2313 ($K_D$=7±2 nM) and (C) DB1976 ($K_D$=5±2 nM) as previously described (Munde et al., 2014). The solid black lines are best fit values for global kinetic fitting of the results with a single binding site function. Similar experiments with DB2115 gave a $K_D$=1±2 nM. The plots are for the SPR signal (RU) versus time from injection of the compound over the sensorchip. From 0 to 180 seconds, compound is being injected (association) and after that only buffer flows over the chip. (B) From top to bottom: 10, 30, 40 nM. (C) From top to bottom: 5, 10, 15 nM.
Figure 8B:
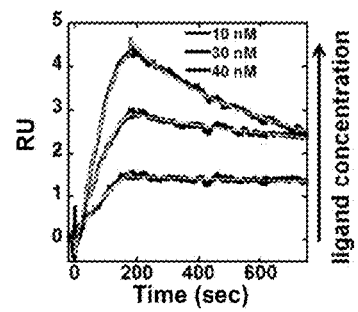
Figure 8C:
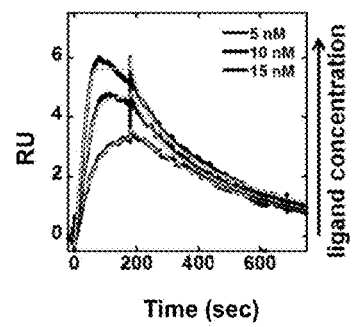

The compounds disclosed herein may be prepared according to the process depicted in FIG. 8.

The compounds disclosed herein may be formulated in a wide variety of compositions for administration to a patient, for instance, a human patient. The compounds disclosed herein are especially useful in treating disease states in elderly patients, i.e., those of sixty years of age or greater. The compounds can be delivered, for example, orally, intravenously, topically, parentally, subcutaneously, intradermally, or by inhalation. Exemplary routes of administration include buccal, oral, intravenous, intramuscular, topical, subcutaneous, rectal, vaginal, parenteral, pulmonary, intranasal, ophthalmic, and the like.

Also provided is a pharmaceutical composition comprising any of the compounds disclosed herein and a pharmaceutically acceptable carrier. The term "carrier" is used in accordance with its art-understood meaning, to refer to a material that is included in a pharmaceutical composition but does not abrogate the biological activity of pharmaceutically active agent(s) that are also included within the composition. Typically, carriers have very low toxicity to the animal to which such compositions are to be administered. In some embodiments, carriers are inert. Pharmaceutically acceptable carriers and diluents that can be used herewith encompasses any of the standard pharmaceutical carriers or diluents, such as, for example, a sterile isotonic saline, phosphate buffered saline solution, water, and emulsions, such as an oil/water or water/oil emulsions.

Also provided is a medicament comprising any of the compounds disclosed herein or any of the pharmaceutical compositions disclosed herein, wherein the compound is in an amount effective to inhibit PU.1.

Also provided is a method of inhibiting PU.1, comprising contacting one or more cells with any of the compounds disclosed herein.

The compounds and compositions disclosed herein may be used to treat diseases associated with abnormal PU.1 levels and activity. The compounds can be used to treat consisting of hematologic cancer, bone cancer, inflammatory disease, inflammatory disorders, autoimmune disorders, endotoxemia and neurodegenerative disease. Exemplary such conditions include leukemia, acute myeloid leukemia, rheumatoid arthritis, contact dermatitis, asthma, inflammatory bowel disease, chronic inflammatory disease, pediatric atrophy, giant cell arteritis, Alzheimer's disease, amyotrophic lateral sclerosis, and systemic lupus. The invention provides a method of treating a patient with a disease associated with abnormal PU.1 function, comprising administering to the patient in need thereof any of the compounds or compositions disclosed herein in an amount effective to inhibit PU.1. The patient can be a human patient or a veterinary patient. The human patient can be, for example, at least 60 years old. As used herein, "treat" a disease means to ameliorate a sign or symptom of the disease, or to cure the patient of the disease.

Useful dosages of the compounds of the invention for inclusion in the pharmaceutical compositions of the invention can be determined by comparing in vitro activity and in vivo activity of the compounds in appropriate animal models. Generally, the concentration of the compound(s) of the invention in a liquid composition will range from about 0.1% to about 95% by weight, preferably from about 0.5% to about 25% by weight. The concentration in a semi-solid or solid composition will range from about 0.1% to 100% by weight, preferably about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The compounds can be co-administered with one or more other agents for the treatment of any of the aforementioned diseases. In certain embodiments, the one or more other agents is a transcription modulator. The one or more other agents can be immunosuppressants. The other agents can be formulated separately, and administered either at the same or different time as the compounds of the instant invention. The other agents can be co-formulated with the compounds of the instant invention to give a combination dosage form.

Disclosed are components that can be used to perform the disclosed methods. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All solvents and reagents were used without purification as acquired from commercial sources. Melting points were measured using a capillary melting point apparatus which are uncorrected. Progress of the chemical reactions were monitored by thin-layer chromatography on silica gel 60-F254 aluminum plates and detected under UV light. All NMR spectra were recorded employing a 400 MHz spectrometer, and chemical shifts (δ) are in ppm relative to TMS as internal standard. Electrospray ionization (ESI) Q-T of and Orbitrap were used for the mass spectra measurements. Elemental analyses are within ±0.4 of the theoretical values.

Compounds reported as salts frequently analyzed for fractional moles of water; the proton NMR showed the presence of the indicated solvent.

Example 1: Synthesis of DB 2313

DB 2313

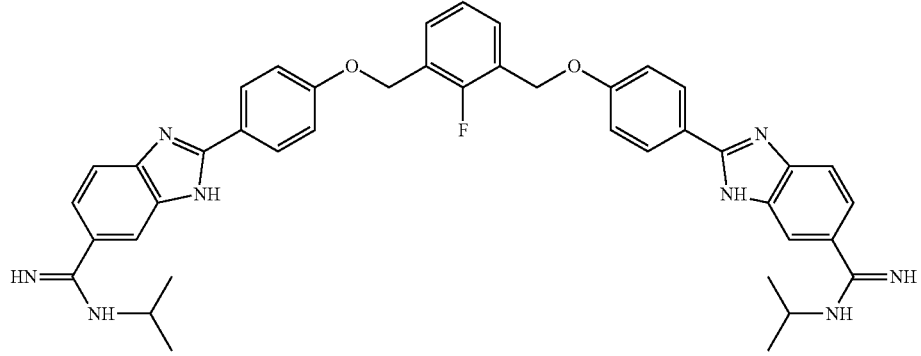

1. 3-Bis (4-formylphenoxymethyl)-2-fluorobenzene

A mixture of 1,3-bis(bromomethyl)-2-fluorobenzene (1.41 g, 0.005 mole), 4-hydroxybenzaldehyde (1.22 g, 0.01 mole) and anhydrous. $K_2CO_3$ (2.07 g, 0.015 mole) in 10 ml DMF was heated at 45° C. for 4 h [tlc (Hexane:EtOAc 8:2) monitored], diluted with ice water 70 ml, the precipitated white solid was filtered, washed with water, and dried. It was dissolved in DCM (75 ml), dried over anhydrous MgSO4, filtered, concentrated and triturated with cold hexane, filtered and dried under reduced pressure to yield a white solid 1.46 g (78%), mp 110-111° C.; $^1$H NMR (DMSO-$d_6$): 9.89 (s, 2H), 7.90 (d, 4H, J=8.4 Hz), 7.62 (t, 2H, J=7.6 Hz), 7.30 (t, 1H, J=7.6 Hz), 7.26 (d, 4H, J=8.4 Hz), 5.31 (s, 4H); $^{13}$C NMR (DMSO-$d_6$): 191.8, 163.5, 159.5 ($J_C$-F=248.6 Hz), 132.3, 131.6 ($J_C$-F=3.7 Hz) 130.5, 125.0 ($J_C$-F=3.7 Hz), 123.9 ($J_C$-F=14.7 Hz) 115.5, 64.4 ($J_C$-F=4.0); MS: HRMS-ESIPOS.: Calcd. For: $C_{22}H_{17}FO_4$ Na m/z 387.1009 ($M^+$+ Na), found m/z 387.1537; Anal. calcd. for: $C_{22}H_{17}FO_4$: C, 72.50; H, 4.70. Found: C, 72.49; H, 4.72.

3-Bis{4[4(5)-N-isopropylamidinobenzimidazolyl]phenoxymethyl]}-2-fluorobenzene tetrahydrochloride A well stirred solution of 1, 3-bis (4-formylphenoxymethyl)-2-fluorobenzene (0.182 g, 0.0005 mole), 4-(N-isopropylamidino)-1, 2-phenylenediamine hydrochloride. $0.2H_2O$ (46) (0.232 g, 0.001 mole) and 1, 4-benzoquinone (0.108 g, 0.001 mole) in anhydrous ethanol (40 ml) (under nitrogen) was heated at reflux for 8-10 h. The reaction mixture was cooled, concentrated to 10 ml and stirred in 50 ml acetone, filtered, washed with dry ether and dried to yield a hydrochloride salt. This salt was dissolved in a 1:1 mixture of hot ethanol-methanol (50 ml) and filtered, volume reduced to 20 ml and acidified with HCl-saturated ethanol (3 ml). After stirring overnight and diluting with anhydrous ether, filtered, washed with ether, and dried under reduced pressure at 70° C. (12 h) yielding purple-bluish grey solid 0.33 g (75%); mp>320° C. dec.; $^1$H NMR (DMSO-$d_6$/65° C.): 9.68 (s, 1H), 9.67 (s, 1H), 9.53 (s, 2H), 9.12 (s, 2H), 8.41 (d, 4H, J=8.4 Hz), 8.08 (s, 2H), 7.86 (d, 2H, J=8.4 Hz), 7.67 (d, 2H, J=8 Hz), 7.65 (d, 2H, J=8 Hz), 7.37-7.32 (m, 5H), 5.34 (s, 4H), 4.10 (quintet, 2H, J=6 Hz), 3.37-3.2 (vbs, benzimidazole NH), 1.31 (d, 12H, J=6 Hz); MS: HRMS-ESI-POS.: calc. for $C_{42}H_{42}FN_8O_2$ m/z 709.3415 ($M^+$+1), found m/z 709.4542; analysis calc. for $C_{42}H_{41}FN_8O_2$.4HCl.1.65$H_2O$: C, 57.14; H, 5.52; N, 12.70. Found: C, 57.35; H, 5.67; N, 12.81.

By analogous methods, DB1976 and DB2115 were also prepared:

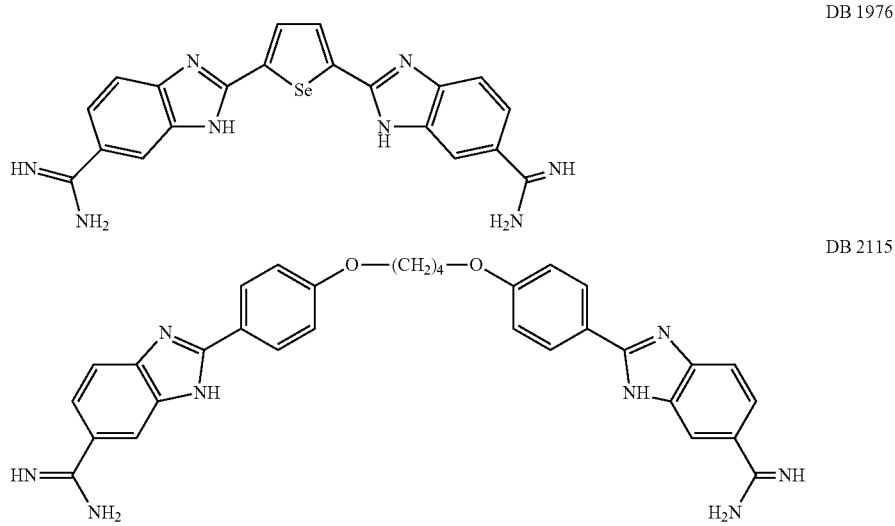

After synthesis DB2115 and DB2313 were dissolved as a 2.5 mM, 70 uM and 33 (mouse cells) or 66 uM (human) uM stock solutions, respectively, in sterile water and stored at −20° C.

Figure 1B:
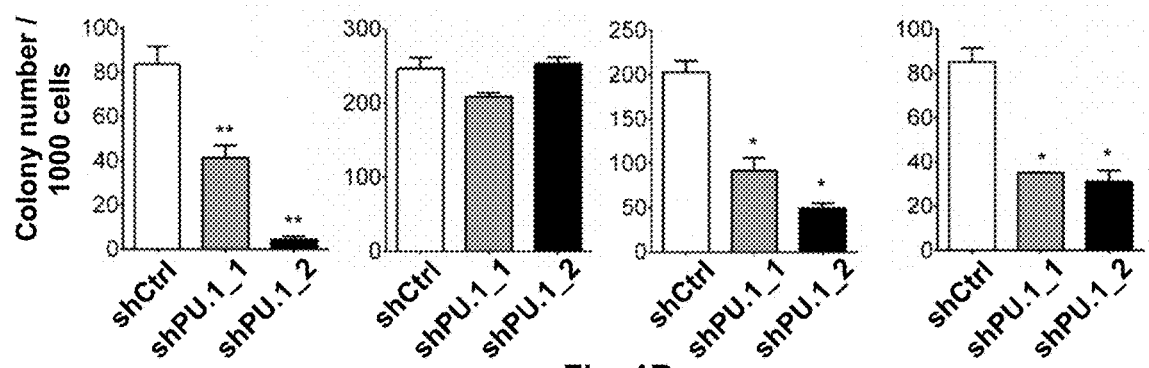
Figure 1C:
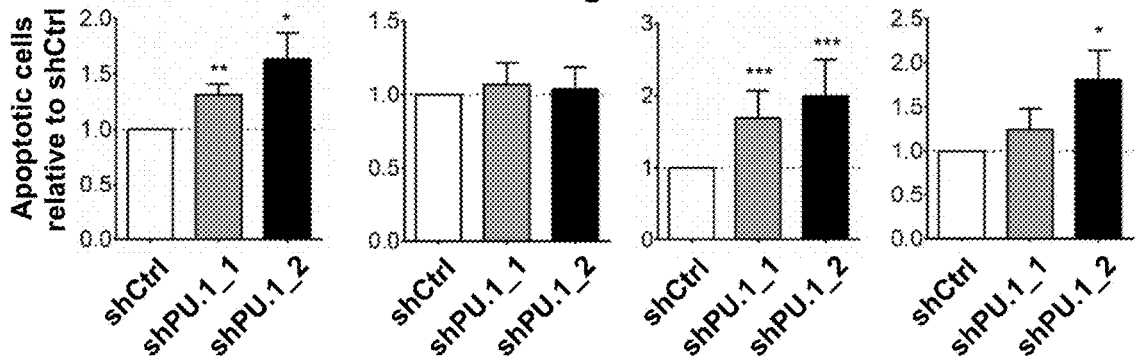

Example 2: PU.1 Knockdown Decreases Cell Growth and Clonogenic Capacity, and Increases Apoptosis of Murine and Human AML Cells To determine whether PU.1 inhibition may be a suitable strategy in AML, we used an established model of AML driven by reduced PU.1 levels, PU.1 URE$^{-/-}$ AML, in which PU.1 expression is reduced to −20% of normal levels by disruption of an upstream enhancer (URE). Knockdown of PU.1 in PU.1 URE$^{-/-}$ AML cells by two different shRNAs led to significantly decreased cell growth and colony formation (FIG. 1A, 1B). Likewise, the percentage of apoptotic cells was significantly increased upon shRNA-mediated PU.1 knockdown in PU.1 URE$^{-/-}$ AML cells (FIG. 1C). The degree of inhibition of growth and clonogenicity, as well as apoptosis induction, were greater with the shRNA leading to more efficient PU.1 knockdown. Knockdown of PU.1 in an immature murine hematopoietic cell line with normal levels of PU.1 (BaF3) did not show significant effects on proliferation or apoptosis.

We next investigated the effect of PU.1 knockdown on human leukemic cell lines with different PU.1 levels. MOLM13 and Kasumi-1 cell lines harbor anomalies associated with low PU.1 levels (FLT3-ITD mutation for MOLM13 and t(8; 21) for Kasumi-1), while THP1 cells have higher PU.1 levels. PU.1 decrease led to a strong growth-inhibitory effect on the growth and clonogenic capacity of MOLM13 and Kasumi-1 cells, whereas it did not have an effect on THP1 cell growth (FIG. 1A, 1B). Accordingly, the apoptotic fraction was significantly increased following PU.1 knockdown in MOLM13 and Kasumi-1 cells, but we observed no effect on THP1 cells (FIG. 1C).

Figures 1D, 1E, 1F:
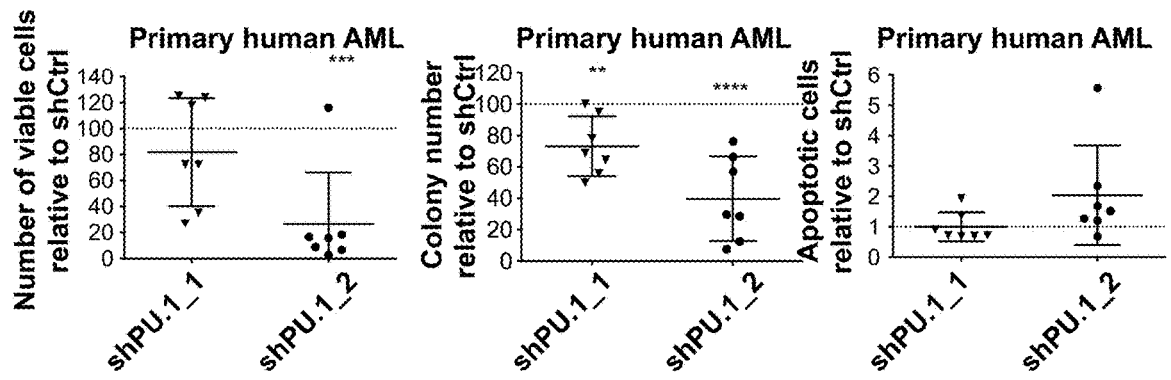

To determine whether PU.1 inhibition has an effect on primary cells from AML patients, we seeded mononuclear cells from AML patients in semi-solid media for 2 weeks and assessed the number of colonies, the number of viable cells and the proportion of apoptotic cells. Knockdown of PU.1 significantly decreased the number of viable cells (mean decrease of 18% for shPU.1_1 and 74% for shPU.1_2) (FIG. 1D), as well as the colony forming capacity of primary human AML cells (mean decrease of 27% for shPU.1_1 and 60% for shPU.1_2, compared to shCtrl) (FIG. 1E). At the same time, the proportion of apoptotic cells increased on average of 2-fold upon knockdown of PU.1 in primary human AML cells with the more efficient shRNA (shPU.1_2) (FIG. 1F).

Taken together, these data show that inhibition of PU.1 decreases cell growth and clonogenic capacity, and increases apoptosis, in murine as well as human AML, and thus provide proof-of-concept for PU.1 inhibition as a possible therapeutic strategy in AML.

Example 3

To test whether these heterocyclic diamidines targeted cognate DNA binding sites for PU.1, we assessed binding to the λB motif by biosensor-surface plasmon resonance (SPR). Duplex DNA harboring the λB motif was immobilized on a streptavidin functionalized sensor chip with a dextran surface as described. The DNA was 5'-end labeled with biotin and captured on the sensor chip. Based on the known strong AT selectivity of these heterocyclic diamidines, they are expected to bind to the AT rich λB promoter sequence at the 5' side of the 5'-GGAA-3' PU.1 conserved recognition sequence. Sensorgrams obtained from the compounds-DNA association and disassociation reactions were used to determine equilibrium dissociation constants. The $K_D$ values indicate strong binding by all three compounds to form a 1:1 complex, and a binding $K^D$ of 1±2 nM for DB2115 and 4-7 nM for DB1976 and DB2313 with the λB promoter.

We next tested the inhibition of PU.1 binding to the λB promoter. Inhibition of the PU.1 complex with λB was monitored by using the same type of sensorchip described for the compound binding experiments. Binding of PU.1 to the immobilized λB DNA was monitored as with the compounds and it was found to form a 1:1 complex with a $K_D$ of 5.4 nM in good agreement with previous results. For the inhibition experiments, recombinant PU.1 was added at a concentration sufficient to occupy >95% of the DNA binding sites. The compounds inhibited PU.1 binding in a concentration dependent manner (FIG. 2B). The dissociation of PU.1 was readily monitored because the compounds have a lower molecular weight than the protein. All three compounds potently inhibited PU.1 binding with $IC_{50}$ values in the low nanomolar range (FIG. 2B). The $IC_{50}$ values are in the order DB2115>DB2313>DB1976. The results show that our compounds have strong binding to the 5'-AT sequence of λB suggesting allosteric inhibition of PU.1 binding.

To probe the allosteric basis of PU.1 inhibition by the three compounds more directly, we performed DNA footprinting experiments on a DNA fragment harboring the λB site with or without the three selected compounds. Since DNase I activity is sensitive to local DNA structure, and both enzyme and compounds target the DNA minor groove, perturbation in the DNase I cleavage pattern would indicate an induced structural effect by the compounds. DNA fragments were saturated with compounds (1 µM) and analyzed by capillary electrophoresis following limited DNase I digests. Relative to the compound-free control, the electropherograms showed significant differences in local DNase I cleavage, in one or both strands, within the AT-rich subsite occupied by the compounds (FIG. 2C). In addition, cleavage patterns at positions distal from the A-rich subsites along the protein/DNA interface were also affected. These perturbations were dependent on the identity of the compound, but in all cases contrasted sharply with the minor groove protection produced by the ETS domain of PU.1. Thus, in addition to partial occlusion of the PU.1/DNA interface, compounds induced distinct DNA conformation and/or dynamic changes that are incompatible with recognition by PU.1.

To test if the inhibition of the PU.1/DNA complex by the compounds resulted in functional inhibition of PU.1 transactivation, we tested the effects of the compounds on the expression of an EGFP reporter under the control of a λM-based PU.1-dependent promoter (FIG. 2D). As quantitatively measured by flow cytometry (FIG. 2E), all three of the selected compounds inhibited PU.1-dependent transactivation in a dose-dependent manner with similar $IC_{50}$ values between 2 to 5 µM (FIG. 2F). Thus, our compounds inhibit the PU.1/DNA complex and its functional activity in live cells, indicating that these compounds permeate into cells and are available in the cell nucleus.

We modelled the interaction of the compounds with DNA by in silico docking studies. As illustrated in FIG. 2G, DB2313 binds to the AT sequence that is on the 5' side of the central 5'-GGAA-3' conserved PU.1 recognition site. PU.1 has a "winged helix" DNA recognition motif with the helix in the major groove at the GGAA and wings that contact the 5' AT sequence as well as the 3' side of GGAA. The model shows DB2313 inserts deeply into the minor groove in a way that locks the DNA structure into a specific conformation. DB2313 has the ability to recognize 10 consecutive base pairs in the minor groove and interacts strongly with the DNA base pair edges at the floor of the minor groove. This interaction interferes with the PU.1 complex in the major groove and causes dissociation of PU.1 in an allosteric process.

Example 4

To determine if our PU.1 inhibitors have an effect on PU.1$^{low}$-induced AML cells, we treated the PU.1 URE$^{-/-}$ AML cell line with compounds at different concentrations. Treatment with the drugs led to a profound decrease in growth of PU.1 URE$^{-/-}$ AML cells after 48 h whereas it had only minimal or no effects on control cells with normal PU.1 levels (BaF3), even at very high doses (FIG. 3A). $IC_{50}$s in PU.1 URE$^{-/-}$ AML ranged in the nanomolar to low micromolar range (DB1976: 25 uM; DB2115: 700 nM; DB 2313: 330 nM). Similarly, treatment of human AML cells with low PU.1 levels (MOLM13) led to significantly decreased cell growth, with no effect on THP1 cells (FIG. 3B). Similar to our observations with PU.1-directed shRNAs, treatment with pharmacological PU.1 inhibitors led to a significant 1.6-, 2- and 3.5-fold increase of apoptotic cells with DB1976, DB2115 and DB2313, respectively, in murine PU.1 URE$^{-/-}$ AML cells (FIG. 3C), and similar effects in human MOLM13 cells.

PU.1 inhibitors also significantly decreased colony forming capacity of PU.1 URE$^{-/-}$ AML and MOLM13 cells, but not of THP1 cells (FIG. 3D). To assess the effect of PU.1 inhibitors on long-term clonogenic capacity (in vitro self-renewal) of PU.1 URE$^{--}$ AML cells, we performed serial replating assays. Strikingly, treatment with DB2313 led to a highly significant decrease of clonogenicity in the second and third rounds of plating, and a complete disruption of clonogenic capacity in the $4^{th}$ and higher rounds of plating (FIG. 3D, right panel).

We also explored the effect of the small molecule PU.1 inhibitors on primary human AML cells, and treated 11 samples from AML patients with PU.1 inhibitors. PU.1 inhibitors led to significant decreases in the number of viable cells (mean decrease: 81% for DB1976, 68% for DB2115, 72% for DB2313) (FIG. 3E), and clonogenic capacity (mean decrease of 36% for DB1976, 45% for DB2115, 60% for DB23313), in comparison to vehicle (FIG. 3F). The apoptotic cell fraction increased on average by 1.5-fold with DB1976, 2.2-fold with DB2115 and 2.5-fold with DB2313 (FIG. 3G). Of note, PU.1 inhibition had an effect on the majority of samples, harboring various genetic and cytogenetic anomalies.

Taken together, treatment with PU.1 inhibitors leads to decreased cell viability, colony formation, and increased apoptosis in PU.1$^{low}$-induced AML cell lines as well as in a majority of primary AML cell samples from patients.

Example 5

To assess on-target activity of our inhibitors in AML cells, we measured transcript levels of well-known PU.1 targets in PU.1 URE$^{-/-}$ AML cells. It has been shown that PU.1 positively regulates Csf1r, Junb, and autoregulates itself, whereas it represses E2f1. In line with this, we found a decrease in Csf1r, Junb, and PU.1 transcript expression and an increase in E2f1 expression upon treatment with DB2115, or DB2313 (FIG. 4A, left panel). As Csf1r is one of the most sensitive PU.1 targets in myeloid cells, we assessed its expression at different time points (1 h, 4 h, 8 h and 24 h) after drug treatment. Interestingly, Csf1r expression significantly decreased as early as 4 h after treatment (FIG. 4A, right panel), in line with a direct effect of the drugs on PU.1 transcriptional activity. Furthermore, treatment of bone marrow mononuclear cells isolated from a PU.1-GFP knock-in reporter mouse model led to a decrease in GFP reporter expression after treatment with DB1976, DB2115, or DB2313, further confirming a direct effect of the compounds on PU.1 transactivation (FIG. 4B), and consistent with PU.1 positive autoregulation. Chromatin-immunoprecipitation (ChIP) assays revealed that treatment of AML cells with DB1976, DB2115 or DB2313 indeed decreased PU.1 occupancy on E2f1, Junb and Csf1r promoters, confirming that the compounds are directly interfering with PU.1 binding to chromatin in vivo (FIG. 4C).

To obtain insight into the genome-wide transcriptional effects following treatment of AML cells with our inhibitors, we performed gene expression analysis. We found dysregulation of 1648 transcripts (out of 34,472 total) by at least 1.2-fold after DB2313 treatment of PU.1 URE$^{-/-}$ AML cells, with 867 probe sets unregulated and 781 probe sets downregulated. We found highly significant enrichment of known genes directly downstream of PU.1 (FIG. 4D). Interestingly, enrichment of genes regulated by other ETS family transcription factors, such as Ets1, Gapbα, Spi-B or Fli-1 was much lower to not significant, suggesting a specific inhibitory effect of our compounds on PU.1 binding, with high selectivity even within the ETS family. We confirmed dysregulation of some known PU.1 target genes such as Ly96, Clec5a, Cdkn1a, Itgb2, Fcgr3 and Gfi1, by qRT-PCR. Top canonical pathways and biological functions with significant enrichment identified by IPA included "hematological system development and function", "cell death and survival", "cellular development", and "cellular growth and proliferation," consistent with known functions of PU.1.

Lastly, we compared the differentially expressed genes upon PU.1 inhibitor treatment of PU.1 URE$^{-/-}$ AML cells with publically available data in which the PU.1 regulatory transcriptional network had been identified by tamoxifen-mediated induction of PU.1 expression in engineered PU.1 null immature hematopoietic cells (PUER) (GSE13125). Of the 1,334 genes dysregulated after PU.1 inhibitor treatment of PU.1 URE$^{-/-}$ AML cells, 36% (484) overlap with previously identified canonical PU.1 targets in PUER cells (FIG. 4E), which is highly significant (p<0.0001). Furthermore, the comparative pathway analysis revealed a significant inverse correlation between PU.1 URE$^{-/-}$ AML cells after treatment and PU.1 overexpression in PUER cells, suggesting that inhibitor treatment antagonizes canonical PU.1-regulated pathways (FIG. 4F). In addition, we performed a comparative analysis with publically available PU.1 ChIP-seq data (GSE63317) and found significant enrichment of PU.1 binding in the promoters of genes deregulated after treatment with PU.1 inhibitor (FIG. 4G). Up- and downregulated genes were similarly affected (FIG. 4G), once again consistent with interference of our drugs with PU.1-chromatin interaction, and independent of downstream transactivating or repressive mechanisms Example 6

In order to determine the effect of our PU.1 inhibitors on normal hematopoietic differentiation, we sorted immature Lin$^-$Sca1$^+$c-Kit$^+$ (LSK) cells from wildtype mice and studied their clonogenic potential following treatment with either DB1976, DB2115, or DB2313. After treatment with PU.1 inhibitors, total numbers of colonies were only slightly reduced; however, we saw a significant reduction of the more mature myelo-monocytic colony types (CFU-GM, CFU-G and CFU-M) (FIG. 5A, right and left panels) and a relative increase in the number of erythroid B/CFU-E and small immature cell colonies (FIG. 5A, left panel), consistent with PU.1's known important role in myelomonocytic differentiation. Of note, one of the compounds (DB1976) appeared to show toxicity on LSK cells, with a majority of colonies unidentifiable and a majority of dead cells, contrary to the 2 other compounds (DB2115, DB2313), which we therefore prioritized for further investigation. Overall, the numbers of viable cells per colony were reduced upon PU.1 inhibitor treatment, again consistent with an effect of PU.1 inhibition on more mature, differentiating cells. Consistently, cytomorphologic analysis revealed almost no macrophages, significantly fewer mature granulocytes, and an increase in immature cells, characterized by a higher nucleo-cytoplasmic ratio and basophilic cytoplasm after treatment (FIG. 5B). This was confirmed by flow cytometric analysis, which revealed a reduction in mature monocytes (CD11b$^+$Gr1$^-$) and granulocytes (CD11b$^+$Gr1$^+$), and a slight increase in immature granulocytes (CD11b$^-$Gr1$^+$) and CD41$^+$ cells, but no significant difference in erythrocyte (Ter119$^+$CD41$^-$) generation (FIG. 5C). To further explore the granulocytic population and pinpoint the exact stage of maturation at which the small molecules impact differentiation, we used a combination of markers and further separated the populations into the myeloblast/promyelocyte-metamyelocyte/mature stages. After treatment, there was a slight increase in the proportion of cells at the myeloblast/promyelocyte stage, a strong increase of metamyelocytes, and a decrease in more mature cells, indicating that our compounds primarily inhibit later stages of granulocytic differentiation.

As we had observed a reduction in mature myelomonocytic colonies upon treatment with PU.1 inhibitors, but persistence or even slight increases in more immature cells (GEMM, and immature colonies), we wanted to test whether these immature cells were still functional after drug removal. We focused on the compound with the lowest IC50 and the least effect on wildtype cells (DB2313). Interestingly, the production of mature granulocytes and monocytes increased significantly by 4-fold and 22-fold, respectively, after removing the treatment in the second plating, showing that the effects of PU.1 inhibition on G/M generation are reversible (FIG. 5D, 5E). In addition, we performed serial replating assays with continuous treatment with PU.1 inhibitors and found no significant differences in terms of serial replating capacity, indicating that treatment with PU.1 inhibitors does not significantly affect long-term colony-forming potential or in vitro self-renewal capacity of immature hematopoietic stem and progenitors (FIG. 5F).

Taken together, these results indicate that treatment with our PU.1 inhibitors leads to effects on normal hematopoiesis consistent with fundamental roles of PU.1 function during hematopoiesis. These effects are reversible upon treatment discontinuation and seem to primarily affect more mature cells.

Figure 6A:
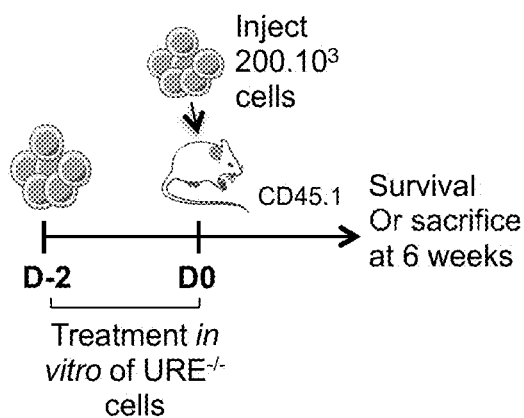
Figure 6B:
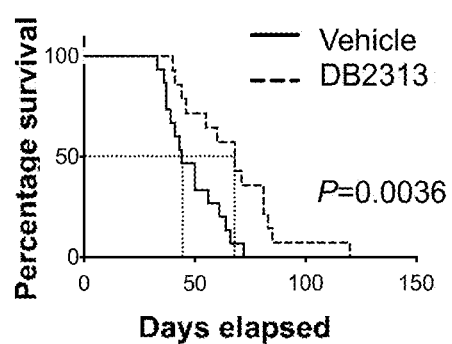
Figure 6C:
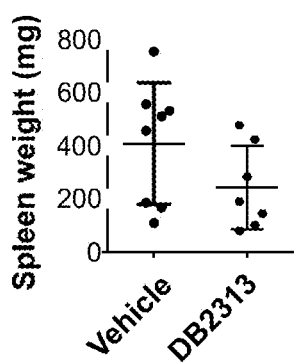
Figure 6D:
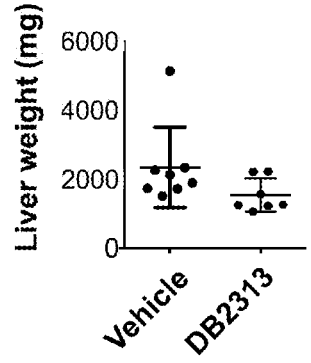
Figure 6E:
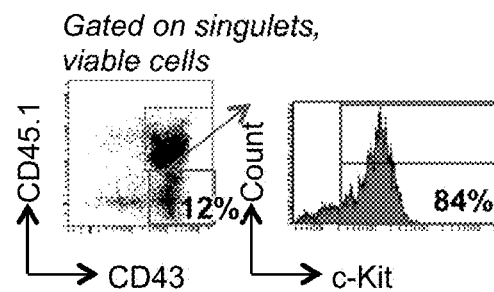
Figure 6F:
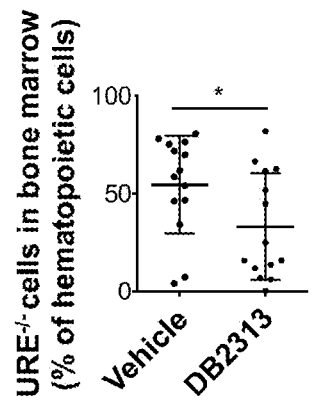
Figure 6G:
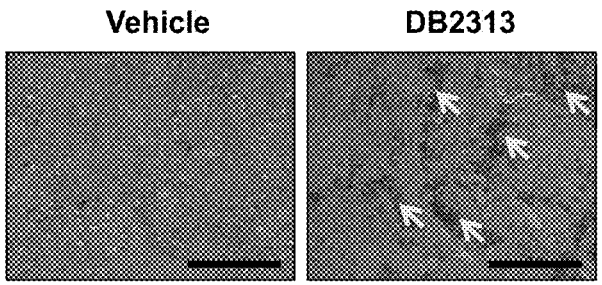
Figure 6H:
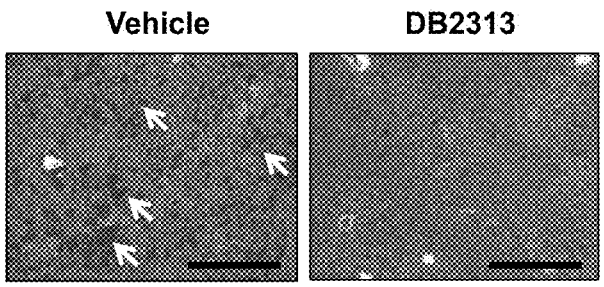
Figure 7:
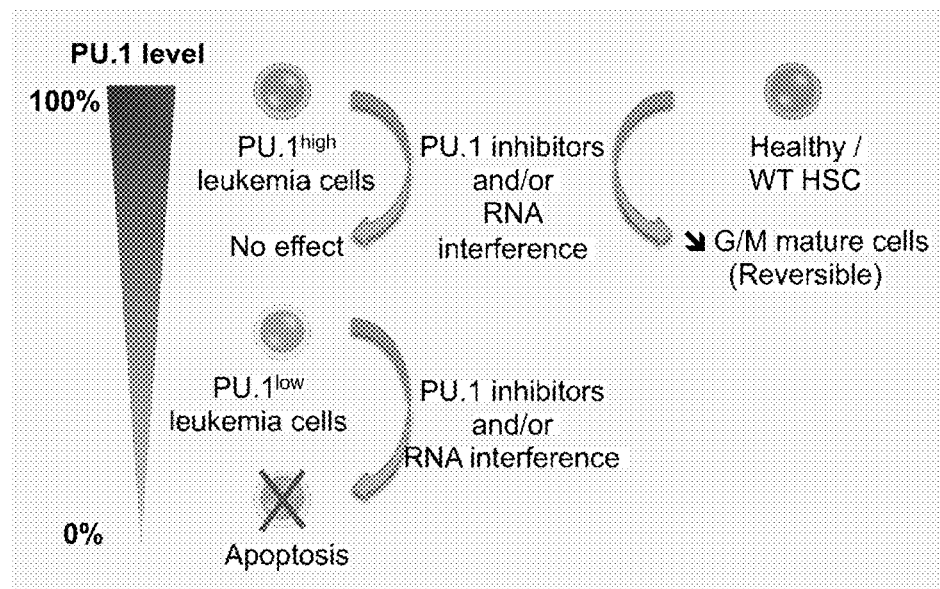
FIG. 7 depicts the effects of PU.1 inhibition of AML and healthy hematopoietic cells.

Example 7: Treatment with PU.1 Inhibitors Decreases Leukemia Progression In Vivo To assess the effect of PU.1 inhibitors on AML in vivo, we treated PU.1 URE$^{-/-}$ AML cells for 2 days in vitro and injected 2×10$^5$ viable cells in sublethally irradiated recipient mice (FIG. 6A). Recipient mice of vehicle-treated AML cells succumbed to leukemia with a median latency of 44 days whereas mice receiving DB2313-treated AML cells survived significantly longer (p=0.0036) with a median latency of 68 days (FIG. 6B). Assessment of tumor burden 6 weeks post transplantation showed a decrease in spleen and liver weights after treatment; splenic mean weight was 410 mg for vehicle and 243 mg for DB2313 (FIG. 6C); liver mean weight was 2,347 mg for vehicle and 1,548 mg for DB2313 (FIG. 6D). AML cell engraftment in the bone marrow was significantly decreased after treatment with DB2313, with a mean chimerism of 55% for the vehicle group and 33% for DB2313 group (FIG. 6E, 6F). Histological analyses revealed severe blast infiltration with disruption of the splenic architecture and virtually complete loss of the red pulp in the vehicle group, and significantly less pronounced effects in the DB2313 group (FIG. 6G). Likewise, infiltration of the liver by leukemic blasts was substantially reduced in the DB2313 group in comparison to the vehicle group (FIG. 6H).

The following compounds were prepared and tested according to the above mentioned methods:

| Code | Structure | $IC_{50}$ URE-/- (μM) | $IC_{50}$ BAF3 (μM) |
|---|---|---|---|
| DB2146 | 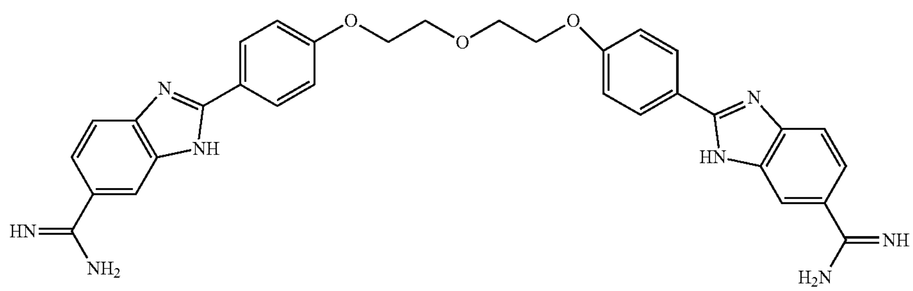 [SMILES: N=C(N)c1ccc2nc(-c3ccc(OCCOCCOc4ccc(-c5nc6ccc(C(=N)N)cc6[nH]5)cc4)cc3)[nH]c2c1] | 5 | 68 |
| DB2150 | 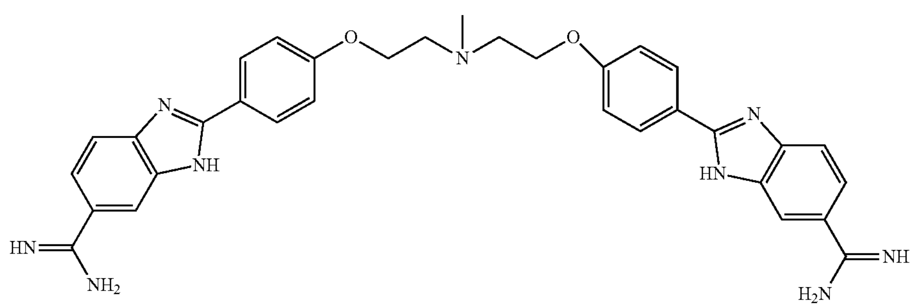 [SMILES: CN(CCOc1ccc(-c2nc3ccc(C(=N)N)cc3[nH]2)cc1)CCOc1ccc(-c2nc3ccc(C(=N)N)cc3[nH]2)cc1] | 20 | 416 |
| DB2237 | 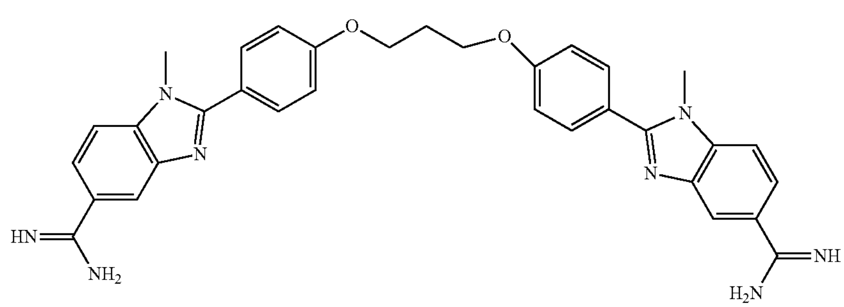 [SMILES: Cn1c(-c2ccc(OCCCOc3ccc(-c4nc5cc(C(=N)N)ccc5n4C)cc3)cc2)nc2cc(C(=N)N)ccc21] | 4.4 | NR |
| DB2295 | 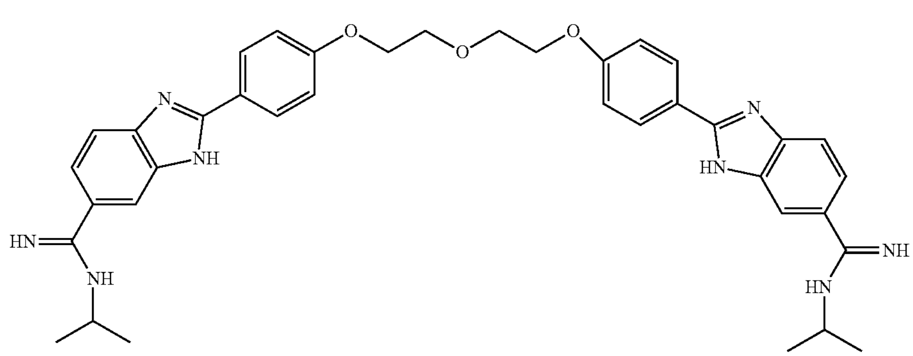 [SMILES: CC(C)NC(=N)c1ccc2nc(-c3ccc(OCCOCCOc4ccc(-c5nc6ccc(C(=N)NC(C)C)cc6[nH]5)cc4)cc3)[nH]c2c1] | 10.5 | NR |

-continued

| Code | Structure | IC$_{50}$ URE-/- (μM) | IC$_{50}$ BAF3 (μM) |
|---|---|---|---|
| DB2302 | 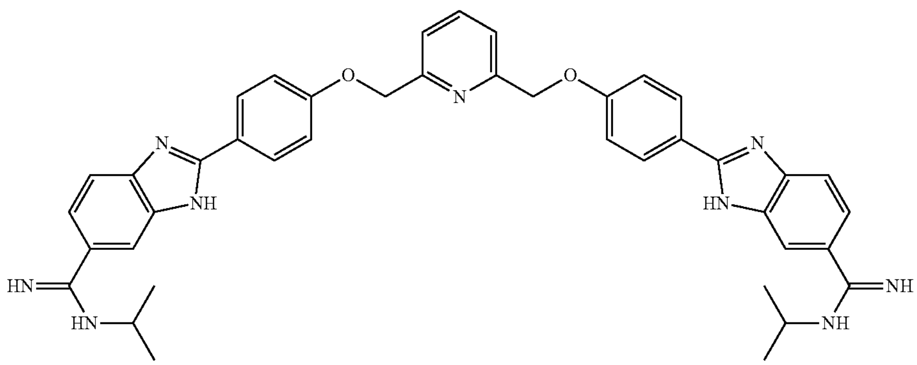 [SMILES: CC(C)NC(=N)c1ccc2nc(-c3ccc(OCc4cccc(COc5ccc(-c6nc7ccc(C(=N)NC(C)C)cc7[nH]6)cc5)n4)cc3)[nH]c2c1] | 7.8 | NR |
| DB2313 | 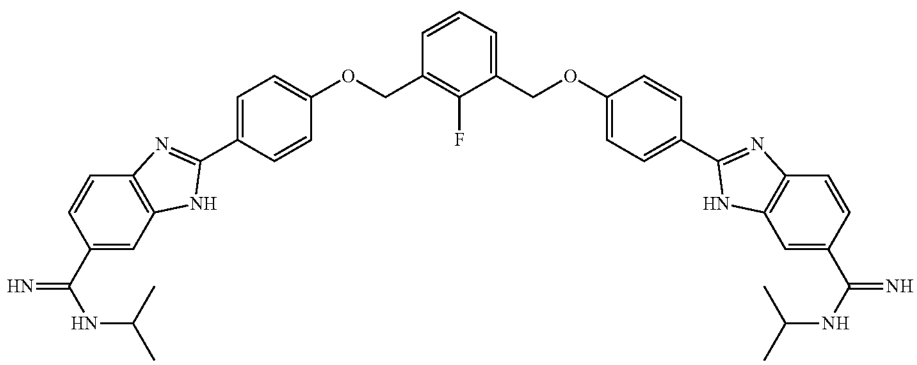 [SMILES: CC(C)NC(=N)c1ccc2nc(-c3ccc(OCc4cccc(COc5ccc(-c6nc7ccc(C(=N)NC(C)C)cc7[nH]6)cc5)c4F)cc3)[nH]c2c1] | 0.33 | NR |
| DB2326 | 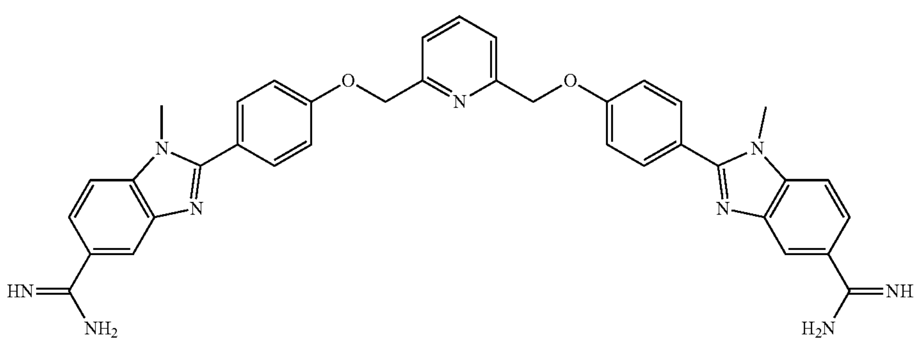 [SMILES: Cn1c(-c2ccc(OCc3cccc(COc4ccc(-c5nc6cc(C(=N)N)ccc6n5C)cc4)n3)cc2)nc2cc(C(=N)N)ccc21] | 1.9 | 48 |
| DB2355 | 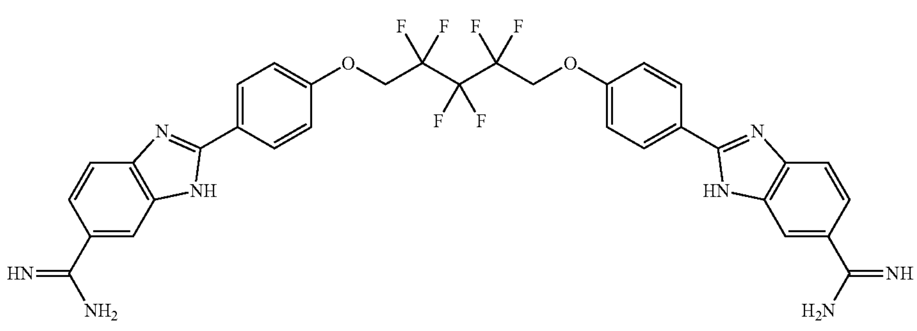 [SMILES: N=C(N)c1ccc2nc(-c3ccc(OCC(F)(F)C(F)(F)C(F)(F)COc4ccc(-c5nc6ccc(C(=N)N)cc6[nH]5)cc4)cc3)[nH]c2c1] | 1.7 | 49 |

| Code | Structure | IC$_{50}$ URE-/- (μM) | IC$_{50}$ BAF3 (μM) |
|---|---|---|---|
| DB2457 | 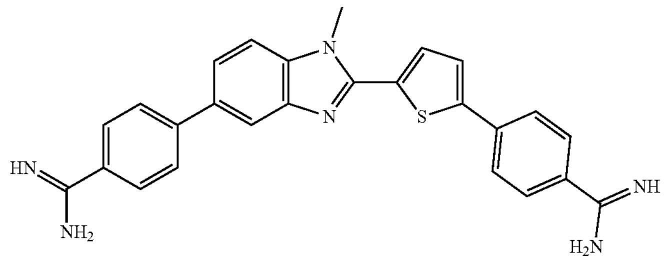 [SMILES: Cn1c(-c2ccc(-c3ccc(C(=N)N)cc3)s2)nc2cc(-c3ccc(C(=N)N)cc3)ccc21] | 16.5 | NR |
| DB2483 | 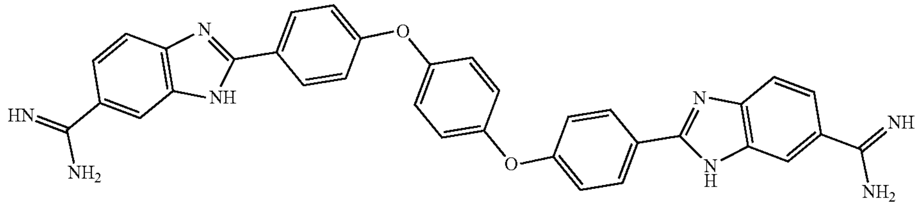 [SMILES: N=C(N)c1ccc2nc(-c3ccc(Oc4ccc(Oc5ccc(-c6nc7ccc(C(=N)N)cc7[nH]6)cc5)cc4)cc3)[nH]c2c1] | 5.3 | NR |
| DB2514 | 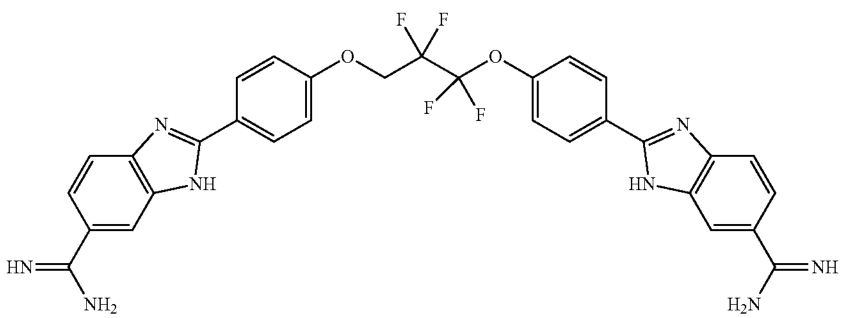 [SMILES: N=C(N)c1ccc2nc(-c3ccc(OCC(F)(F)C(F)(F)Oc4ccc(-c5nc6ccc(C(=N)N)cc6[nH]5)cc4)cc3)[nH]c2c1] | 5.6 | 44.5 |

NR = Not Reached

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

REFERENCES

Munde, M., Wang, S., Kumar, A., Stephens, C. E., Farahat, A. A., Boykin, D. W., Wilson, W. D., and Poon, G. M. K. (2014) Inhibition of the ETS-family transcription factor PU.1 by heterocyclic diamidines. Nucleic Acids Research. 42: 1379-90.

What is claimed is:

1. A compound having the formula:

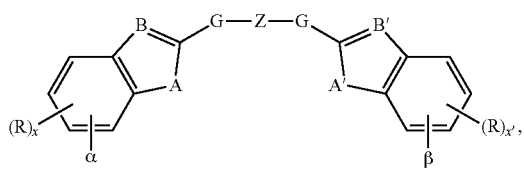

or a pharmaceutically acceptable salt thereof, wherein:

x and x' are each 3;

R is in each case independently selected from the group consisting of $R^a$, $OR^a$, $N(R^a)_2$, $SR^a$, $SO_2R^a$, $SO_2N(R^a)_2$, $COOR^a$, $C(O)N(R^a)_2$, $OC(O)N(R^a)_2$, $N(R^a)C(O)N(R^a)_2$, F, Cl, Br, I, cyano, and nitro, wherein $R^a$ is in each case independently selected from the group consisting of hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^a$ may together form a ring;

G and G' are independently selected from $C_{3-8}$ cycloalkyl, $C_{2-8}$ heterocyclyl, $C_{6-12}$ aryl, and $C_{3-12}$ heteroaryl, wherein each $C_{6-12}$ aryl is optionally and independently substituted with $R^8$ or $R^9$;

A and A' are independently selected from the group consisting of $NR^1$, O, S, and Se, wherein $R^1$, when present, is in each case independently selected from the group consisting of $R^b$, $SO_2R^b$, $SO_2N(R^b)_2$, $COOR^b$, and $C(O)N(R^b)_2$, wherein $R^b$ is in each case independently selected from the group consisting of hydrogen, $C_{1-8}$ alkyl, $C_{3-8}$ cycloalkyl, $C_{2-8}$ heterocyclyl, $C_{6-12}$ aryl, and $C_{3-12}$ heteroaryl, wherein any two or more of R and $R^1$ may together form a ring;

B and B' are independently selected from the group consisting of N and CR;

α has the formula:

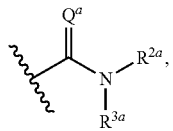

wherein $Q^a$ is O or $NR^{1a}$, wherein $R^{1a}$, $R^{2a}$, and $R^{3a}$ are independently selected from the group consisting of hydrogen, $C_{1-8}$ alkyl, $C_{3-8}$ cycloalkyl, and $C_{2-8}$ heterocyclyl; wherein any two or more of $R^{1a}$, $R^{2a}$, $R^{3a}$, R and $R^1$ can together form a ring;

β has the formula:

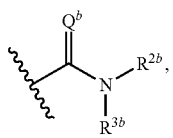

wherein $Q^b$ is O or $NR^{1b}$, wherein $R^{1b}$, $R^{2b}$, and $R^{3b}$ are independently selected from hydrogen, $C_{1-8}$ alkyl, $C_{3-8}$ cycloalkyl, and $C_{2-8}$ heterocyclyl; wherein any two or more of $R^{1b}$, $R^{2b}$, and $R^{3b}$, R and $R^1$ can together form a ring;

wherein $Q^a$ and $Q^b$ are not both O;

Z is (a) a linking group having the formula:

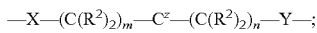

wherein X and Y are independently selected from the group consisting of O, S, Se, and $NR^4$; wherein $R^4$, when present, is in each case independently selected from the group consisting of $R^c$, $SO_2R^c$, $SO_2N(R^c)_2$, $COOR^c$, and $C(O)N(R^c)_2$, wherein $R^c$ is in each case independently selected from the group consisting of hydrogen, $C_{1-8}$ alkyl, $C_{3-8}$ cycloalkyl, $C_{2-8}$ heterocyclyl, $C_{6-12}$ aryl, and $C_{3-12}$ heteroaryl;

$R^2$ is in each case independently H or F;

m and n are each an integer independently selected from 0-4;

$C^z$ is selected from O, S, Se, $NR^4$, $C_{3-8}$ cycloalkyl, $C_{2-8}$ heterocyclyl, $C_{6-12}$ aryl, and $C_{3-12}$ heteroaryl;

or (b) $X-(C(R^5)_2)_m-C^z-(C(R^5)_2)_n-Y-$, wherein X and Y are independently selected from the group consisting of O, S, Se, and $NR^4$, wherein $R^4$, m and n are as defined in (a), wherein $C^z$ is a chemical bond, wherein $R^5$ is in each case independently H or F and at least one $R^5$ is F, and wherein the sum of m and n is greater than 2;

$R^8$=H or $R^9$;

$R^9$=$O(CH_2)n^aN(R^{10})_2$ or $O(CH_2)n^aNH (C=NH)NH_2$;

$R^{10}$=$C_1$-$C_6$ alkyl or cyclo-alkyl; and $n^a$=2-8.

2. The compound according to claim 1, wherein $C^z$ in (a) of Z is a group of the formula:

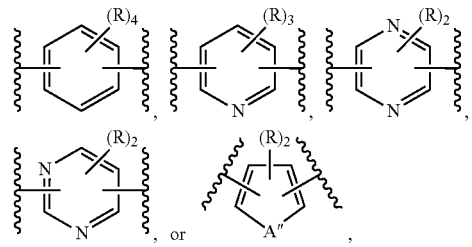

wherein A" is O, S, Se, or $NR^6$; wherein $R^6$ is hydrogen, $C_{1-8}$alkyl; $C_{3-8}$ cycloalkyl, and $C_{2-8}$ heterocyclyl.

3. The compound according to claim 1, wherein Z is as defined in (a), and X and Y are both O.

4. The compound according to claim 1, wherein B and B' are both N.

5. The compound according to claim 1, wherein A and A' are both $NR^4$.

6. The compound according to claim 1, having the formula:

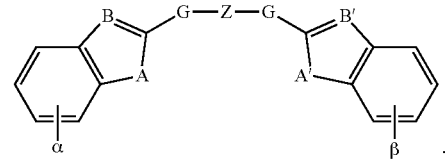

7. The compound according to claim 1, wherein α is in the 7 position.

8. The compound according to claim 1, wherein α is in the 4, 5 or 6 position.

9. The compound according to claim 1, wherein β is in the 7 position.

10. The compound according to claim 1, wherein β is in the 4, 5 or 6 position.

11. The compound according to claim 1, wherein $C^z$ in (a) of Z is:

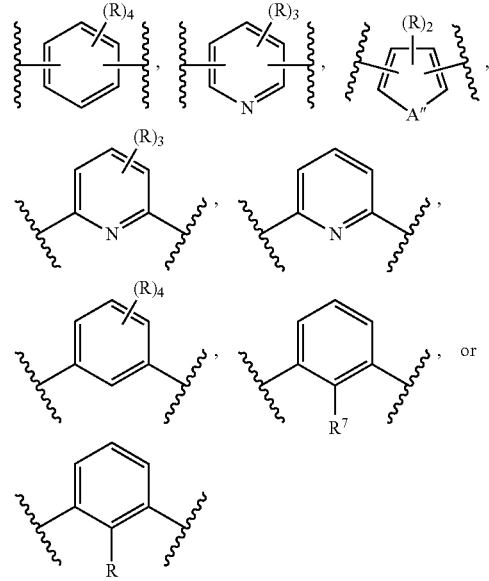

wherein R is selected from the group consisting of hydrogen, F, Cl, Br, I, cyano and nitro, wherein A" is selected from the group consisting of O, S, Se, and $NR^6$; wherein $R^6$ is selected from the group consisting of hydrogen, $C_{1-8}$alkyl; $C_{3-8}$ cycloalkyl, and $C_{2-8}$ heterocyclyl; and wherein $R^7$ is selected from the group consisting of R, hydrogen, F, Cl, Br, I, cyano and nitro.

12. The compound according to claim 1, wherein $C^z$ is O or $NR^4$.

13. The compound according to claim 1, wherein $C^z$ is $NR^4$, wherein $R^4$ is $C_{1-4}$ alkyl.

14. The compound according to claim 1, wherein $C_z$ is a chemical bond.

15. The compound according to claim 1, wherein Z is selected from the group consisting of O—$CH_2$—$CF_2$—$CF_2$—$CF_2$—$CH_2$—O—, O—$CH_2$—$CF_2$—$CF_2$—O—, —O—$CF_2$—$CF_2$—$CF_2$—O—, and —O—$CH_2$—$CF_2$—$CH_2$—O—.

16. The compound according to claim 1, wherein α has the formula:

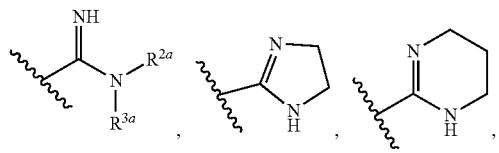

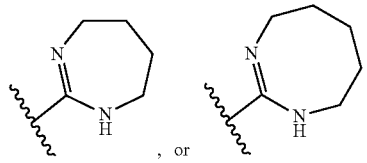, or 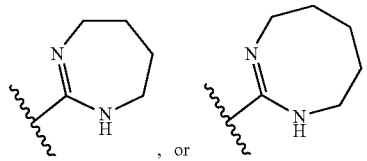.

17. The compound according to claim 1, wherein β has the formula:

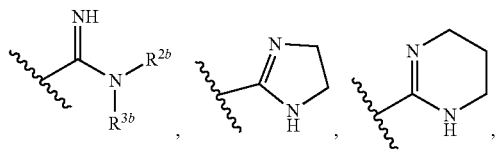

, or .

18. The compound according to claim 1, wherein the compound is selected from the group consisting of:

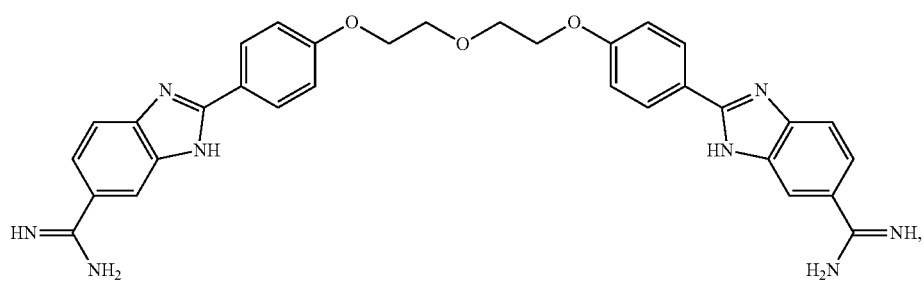

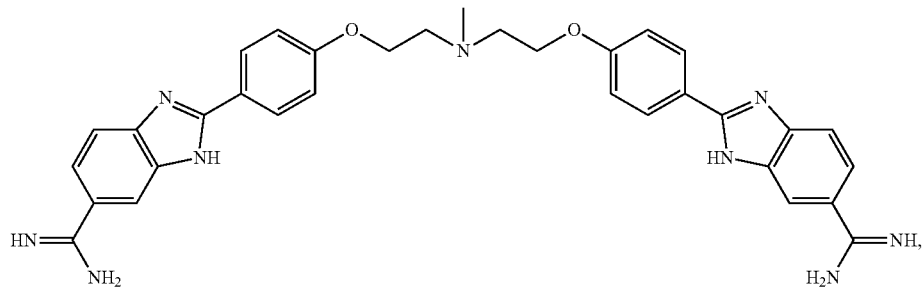

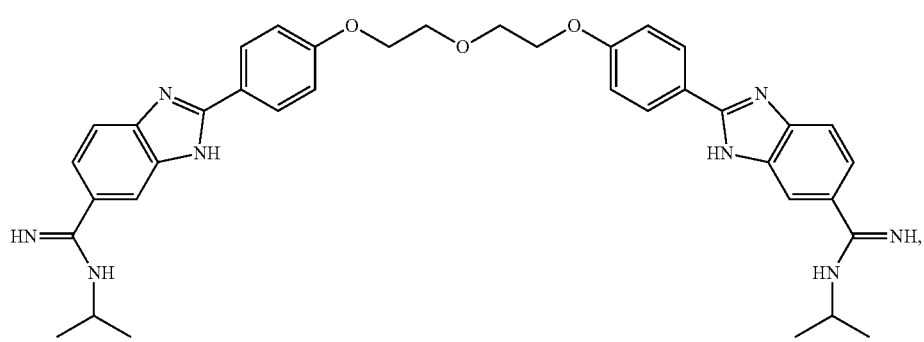

-continued
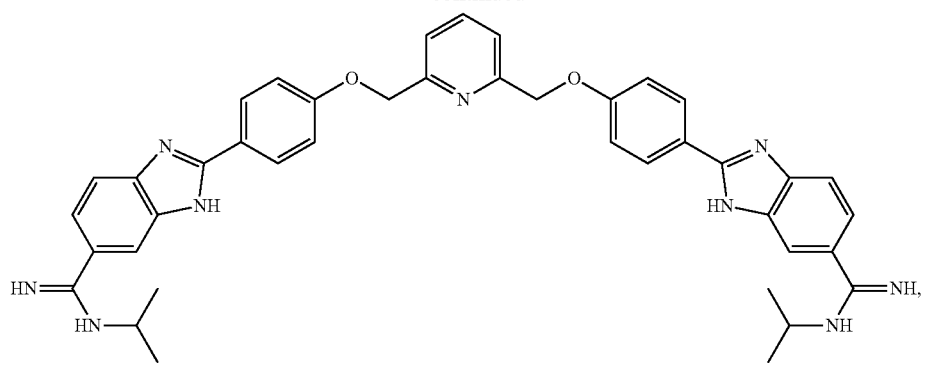
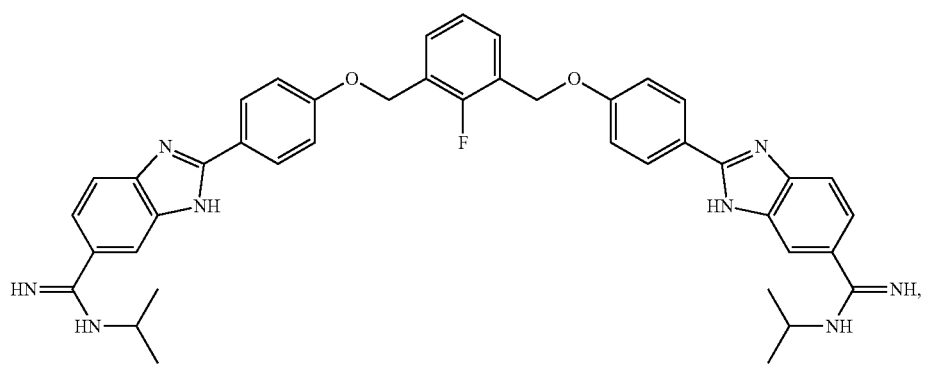
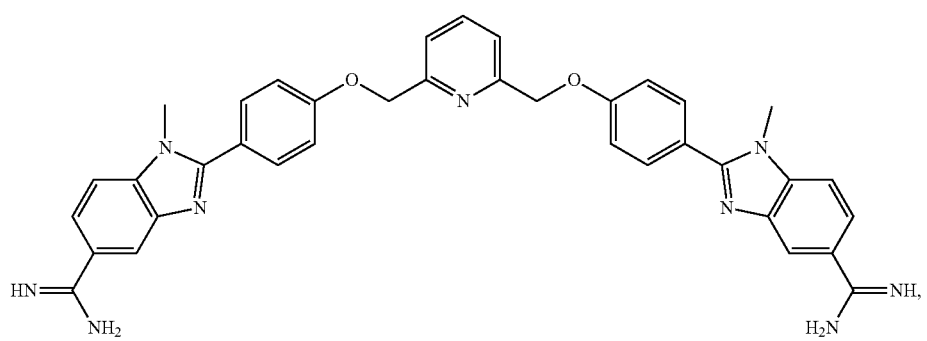
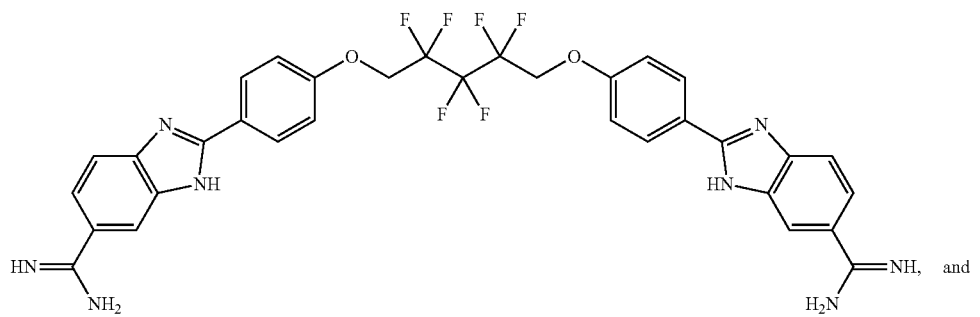
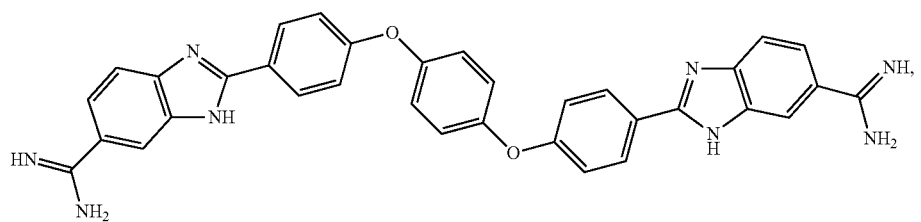

-continued

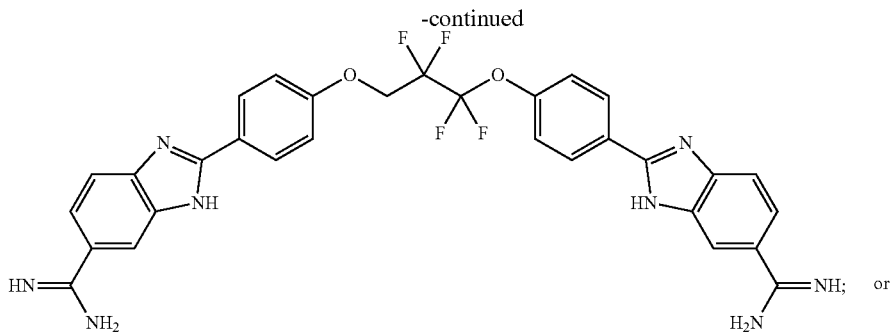

or
a pharmaceutically acceptable salt thereof.

19. A pharmaceutical composition comprising the compound of claim 1 and a pharmaceutically acceptable carrier.

20. A method of inhibiting PU.1, comprising contacting one or more cells with a compound according to claim 1.

21. A method of ameliorating a symptom of a disease associated with abnormal PU.1 function in a patient, comprising administering to the patient in need thereof the compound of claim 1 in an amount effective to inhibit PU.1.

22. The method according to claim 21, wherein the disease is selected from the group consisting of hematologic cancer, bone cancer, inflammatory disease, autoimmune disorders, endotoxemia neurodegenerative disease, leukemia, acute myeloid leukemia, rheumatoid arthritis, contact dermatitis, asthma, inflammatory bowel disease, chronic inflammatory disease, pediatric atropy, giant cell arteritis, Alzheimer's disease, amyotrophic lateral sclerosis and systemic lupus.

23. The method according to claim 21, wherein the patient is a human at least sixty years old.

24. The compound according to claim 1, wherein Z is as defined in (b), and X and Y are both O.

25. The compound of claim 1, which represented by the formula:

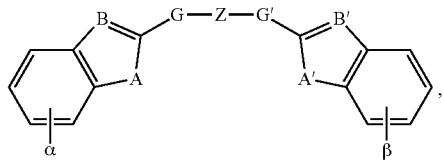

wherein
A and A' are each NH;
B and B' are each N;
α has the formula:

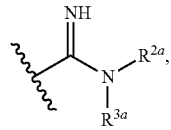

wherein $R^{2a}$ and $R^{3a}$ are each hydrogen;
β has the formula:

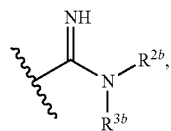

wherein $R^{2b}$ and $R^{3b}$ are each hydrogen;
wherein α and β groups are each in the 5 or 6 position;
G and G' are independently phenyl substituted with $R^9$.

26. The compound of claim 25, wherein α and β groups are each in the 6 position.

27. A compound, which is

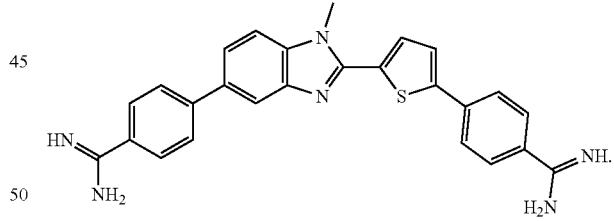

* * * * *

SEQUENCE LISTING

<160> NUMBER OF SEQ ID NOS: 4

<210> SEQ ID NO 1

<211> LENGTH: 270
<212> TYPE: PRT
<213> ORGANISM: Homo sapiens

<400> SEQUENCE: 1

```
Met Leu Gln Ala Cys Lys Met Glu Gly Phe Pro Leu Val Pro Pro
1               5                   10                  15

Ser Glu Asp Leu Val Pro Tyr Asp Thr Asp Leu Tyr Gln Arg Gln Thr
            20                  25                  30

His Glu Tyr Tyr Pro Tyr Leu Ser Ser Asp Gly Glu Ser His Ser Asp
        35                  40                  45

His Tyr Trp Asp Phe His Pro His His Val His Ser Glu Phe Glu Ser
    50                  55                  60

Phe Ala Glu Asn Asn Phe Thr Glu Leu Gln Ser Val Gln Pro Pro Gln
65                  70                  75                  80

Leu Gln Gln Leu Tyr Arg His Met Glu Leu Glu Gln Met His Val Leu
                85                  90                  95

Asp Thr Pro Met Val Pro Pro His Pro Ser Leu Gly His Gln Val Ser
            100                 105                 110

Tyr Leu Pro Arg Met Cys Leu Gln Tyr Pro Ser Leu Ser Pro Ala Gln
        115                 120                 125

Pro Ser Ser Asp Glu Glu Gly Glu Arg Gln Ser Pro Pro Leu Glu
    130                 135                 140

Val Ser Asp Gly Glu Ala Asp Gly Leu Glu Pro Gly Pro Gly Leu Leu
145                 150                 155                 160

Pro Gly Glu Thr Gly Ser Lys Lys Lys Ile Arg Leu Tyr Gln Phe Leu
                165                 170                 175

Leu Asp Leu Leu Arg Ser Gly Asp Met Lys Asp Ser Ile Trp Trp Val
            180                 185                 190

Asp Lys Asp Lys Gly Thr Phe Gln Phe Ser Ser Lys His Lys Glu Ala
        195                 200                 205

Leu Ala His Arg Trp Gly Ile Gln Lys Gly Asn Arg Lys Lys Met Thr
    210                 215                 220

Tyr Gln Lys Met Ala Arg Ala Leu Arg Asn Tyr Gly Lys Thr Gly Glu
225                 230                 235                 240

Val Lys Lys Val Lys Lys Lys Leu Thr Tyr Gln Phe Ser Gly Glu Val
                245                 250                 255

Leu Gly Arg Gly Gly Leu Ala Glu Arg Arg His Pro His
            260                 265                 270
```

<210> SEQ ID NO 2
<211> LENGTH: 271
<212> TYPE: PRT
<213> ORGANISM: Homo sapiens

<400> SEQUENCE: 2

```
Met Leu Gln Ala Cys Lys Met Glu Gly Phe Pro Leu Val Pro Pro Gln
1               5                   10                  15

Pro Ser Glu Asp Leu Val Pro Tyr Asp Thr Asp Leu Tyr Gln Arg Gln
            20                  25                  30

Thr His Glu Tyr Tyr Pro Tyr Leu Ser Ser Asp Gly Glu Ser His Ser
        35                  40                  45

Asp His Tyr Trp Asp Phe His Pro His His Val His Ser Glu Phe Glu
    50                  55                  60

Ser Phe Ala Glu Asn Asn Phe Thr Glu Leu Gln Ser Val Gln Pro Pro
65                  70                  75                  80
```

```
Gln Leu Gln Gln Leu Tyr Arg His Met Glu Leu Gln Met His Val
            85                  90                  95
Leu Asp Thr Pro Met Val Pro Pro His Pro Ser Leu Gly His Gln Val
            100                 105             110
Ser Tyr Leu Pro Arg Met Cys Leu Gln Tyr Pro Ser Leu Ser Pro Ala
            115             120                 125
Gln Pro Ser Ser Asp Glu Glu Glu Gly Glu Arg Gln Ser Pro Pro Leu
    130                 135                 140
Glu Val Ser Asp Gly Glu Ala Asp Gly Leu Glu Pro Gly Pro Gly Leu
145             150                 155                 160
Leu Pro Gly Glu Thr Gly Ser Lys Lys Lys Ile Arg Leu Tyr Gln Phe
                165                 170                 175
Leu Leu Asp Leu Leu Arg Ser Gly Asp Met Lys Asp Ser Ile Trp Trp
            180                 185                 190
Val Asp Lys Asp Lys Gly Thr Phe Gln Phe Ser Ser Lys His Lys Glu
            195                 200                 205
Ala Leu Ala His Arg Trp Gly Ile Gln Lys Gly Asn Arg Lys Lys Met
    210                 215                 220
Thr Tyr Gln Lys Met Ala Arg Ala Leu Arg Asn Tyr Gly Lys Thr Gly
225                 230                 235                 240
Glu Val Lys Lys Val Lys Lys Lys Leu Thr Tyr Gln Phe Ser Gly Glu
                245                 250                 255
Val Leu Gly Arg Gly Gly Leu Ala Glu Arg Arg His Pro Pro His
                260                 265                 270

<210> SEQ ID NO 3
<211> LENGTH: 14
<212> TYPE: DNA
<213> ORGANISM: Mus musculus

<400> SEQUENCE: 3
aaataaagga agtg                                                14

<210> SEQ ID NO 4
<211> LENGTH: 14
<212> TYPE: DNA
<213> ORGANISM: Mus musculus

<400> SEQUENCE: 4
cacttccttt tatt                                                14
```